(12) United States Patent
Chalk et al.

(10) Patent No.: US 12,111,951 B2
(45) Date of Patent: Oct. 8, 2024

(54) SYSTEMS AND METHODS FOR DATASET RECOMMENDATION IN A ZERO-TRUST COMPUTING ENVIRONMENT

(71) Applicant: BeeKeeperAI, Inc., Austin, TX (US)

(72) Inventors: Mary Elizabeth Chalk, Austin, TX (US); Robert Derward Rogers, Oakland, CA (US)

(73) Assignee: BeeKeeperAI, Inc., Austin, TX (US)

( * ) Notice: Subject to any disclaimer, the term of this patent is extended or adjusted under 35 U.S.C. 154(b) by 0 days.

(21) Appl. No.: 18/169,867

(22) Filed: Feb. 15, 2023

(65) Prior Publication Data

US 2023/0273931 A1 Aug. 31, 2023

Related U.S. Application Data

(63) Continuation of application No. 18/169,111, filed on Feb. 14, 2023, and a continuation of application No.
(Continued)

(51) Int. Cl.
*G06F 16/22* (2019.01)
*G06F 16/2458* (2019.01)
(Continued)

(52) U.S. Cl.
CPC ...... *G06F 21/6245* (2013.01); *G06F 16/2237* (2019.01); *G06F 16/2458* (2019.01);
(Continued)

(58) Field of Classification Search
CPC ............. G06F 16/2237; G06F 16/2458; G06F 16/2462; G06F 16/334; G06F 16/3347; G06F 16/56

See application file for complete search history.

(56) References Cited

U.S. PATENT DOCUMENTS

2002/0174086 A1* 11/2002 Verma .................... G06F 18/256
2005/0075846 A1* 4/2005 Kim ...................... G01N 29/245
703/1
(Continued)

FOREIGN PATENT DOCUMENTS

WO WO-2022072892 A1 * 4/2022 ......... G06F 21/6218

OTHER PUBLICATIONS

ISA/US, "Notification of Transmittal of the ISR and the Written Opinion of the International Searching Authority, or the Declaration," in PCT Application No. PCT/US2023/063083, Jul. 24, 2023, 16 pages.

*Primary Examiner* — James E Richardson
(74) *Attorney, Agent, or Firm* — Kang S. Lim

(57) ABSTRACT

Systems and methods for recommendation of cohort sample sets is provided. In some embodiments, a set of dataset requirements is received as a required vector set. The historical vector sets are queried. Each vector set corresponds to a known dataset. The difference between the required vector set and each of the historical vector sets is calculated by framing the distance as a p-value in a hypothesis test, compared against a threshold. The historical vector set with the least difference to the required vector set is identified. The least difference is calculated as a count of differing classes or as a numerically weighted summation of differing classes.

18 Claims, 24 Drawing Sheets

Related U.S. Application Data

18/169,122, filed on Feb. 14, 2023, said application No. 18/169,111 is a continuation of application No. 18/168,560, filed on Feb. 13, 2023, said application No. 18/169,122 is a continuation of application No. 18/168,560, filed on Feb. 13, 2023.

(60) Provisional application No. 63/313,774, filed on Feb. 25, 2022.

(51) Int. Cl.
*G06F 21/60* (2013.01)
*G06F 21/62* (2013.01)
*G16H 50/70* (2018.01)

(52) U.S. Cl.
CPC ........ *G06F 16/2462* (2019.01); *G06F 21/602* (2013.01); *G16H 50/70* (2018.01); *G06F 2221/2115* (2013.01)

(56) References Cited

U.S. PATENT DOCUMENTS

| | | | |
|---|---|---|---|
| 2008/0235575 A1* | 9/2008 | Weiss | G06F 16/51 707/E17.031 |
| 2015/0142807 A1* | 5/2015 | Hofmann | G06N 3/044 707/759 |
| 2017/0068477 A1 | 3/2017 | Yu | |
| 2018/0018590 A1* | 1/2018 | Szeto | G16H 50/20 |
| 2018/0114142 A1 | 4/2018 | Mueller et al. | |
| 2018/0165418 A1* | 6/2018 | Swartz | G16H 50/70 |
| 2020/0111019 A1 | 4/2020 | Goodsitt et al. | |
| 2020/0311607 A1* | 10/2020 | Mestres | G06Q 30/0203 |
| 2020/0322820 A1 | 10/2020 | Carter et al. | |
| 2020/0402625 A1* | 12/2020 | Aravamudan | G06F 21/64 |
| 2021/0041906 A1* | 2/2021 | Ikarashi | H04L 9/085 |
| 2021/0092160 A1 | 3/2021 | Crabtree et al. | |
| 2021/0141940 A1* | 5/2021 | Naqvi | G06F 21/602 |
| 2021/0173854 A1 | 6/2021 | Wilshinsky | |
| 2021/0294840 A1* | 9/2021 | Lee | G06N 3/084 |
| 2022/0021711 A1 | 1/2022 | Marsh et al. | |
| 2023/0030479 A1* | 2/2023 | Reimann | G01N 21/31 |
| 2023/0061341 A1* | 3/2023 | Shmueli | G06F 16/2237 |
| 2023/0161811 A1* | 5/2023 | Peng | G06F 16/56 707/749 |

* cited by examiner

SYSTEMS AND METHODS FOR DATASET RECOMMENDATION IN A ZERO-TRUST COMPUTING ENVIRONMENT

CROSS REFERENCED TO RELATED APPLICATIONS

This non-provisional application claims the benefit and priority of U.S. non-Provisional application Ser. No. 18/168,560, filed on Feb. 13, 2023, entitled "Systems And Methods For Dataset Selection Optimization In A Zero-Trust Computing Environment", which also claims priority to U.S. provisional application No. 63/313,774, filed on Feb. 25, 2022, entitled "Systems And Methods For Dataset Selection Optimization, Verification And Recommendation", the contents of which are incorporated herein in their entirety by this reference.

This application claims the benefit and priority of U.S. non-Provisional application Ser. No. 18/169,122, filed on Feb. 14, 2023, entitled "Systems And Methods For Dataset Quality Quantification In A Zero-Trust Computing Environment" and U.S. non-Provisional application Ser. No. 18/169,111, filed on Feb. 14, 2023, entitled "Systems And Methods For Dataset Verification In A Zero-Trust Computing Environment", the contents of which are incorporated herein by references in their entirety.

BACKGROUND

The present invention relates in general to the field of cohort selection within a zero-trust computing environment, and more specifically to methods, computer programs and systems for providing selection, verification and recommendations of patient datasets to a data consumer without exposing the datasets prior to their selection. Such systems and methods are particularly useful in situations where the data is highly sensitive, such a protected health information.

Within certain fields, there is a distinguishment between the developers of algorithms (or other data consumer entities), and the stewards of the data that said algorithms are intended to operate with and be trained by. On its surface this seems to be an easily solved problem of merely sharing either the algorithm or the data that it is intended to operate with. However, in reality, there is often a strong need to keep the data and the algorithm secret. For example, the companies developing their algorithms may have the bulk of their intellectual property tied into the software comprising the algorithm. For many of these companies, their entire value may be centered in their proprietary algorithms. Sharing such sensitive data is a real risk to these companies, as the leakage of the software base code could eliminate their competitive advantage overnight.

One could imagine that instead, the data could be provided to the algorithm developer for running their proprietary algorithms and generation of the attendant reports. However, the problem with this methodology is two-fold. Firstly, often the datasets for processing and extremely large, requiring significant time to transfer the data from the data steward to the algorithm developer. Indeed, sometimes the datasets involved consume petabytes of data. The fastest fiber optics internet speed in the US is 2,000 MB/second. At this speed, transferring a petabyte of data can take nearly seven days to complete. It should be noted that most commercial internet speeds are a fraction of this maximum fiber optic speed.

The second reason that the datasets are not readily shared with the algorithm developers is that the data itself may be secret in some manner. For example, the data could also be proprietary, being of a significant asset value. Moreover, the data may be subject to some control or regulation. This is particularly true in the case of medical information. Protected health information, or PHI, for example, is subject to a myriad of laws, such as HIPAA, that include strict requirements on the sharing of PHI, and are subject to significant fines if such requirements are not adhered to.

Healthcare related information is of particular focus of this application. Of all the global stored data, about 30% resides in healthcare. This data provides a treasure trove of information for algorithm developers to train their specific algorithm models (AI or otherwise), and allows for the identification of correlations and associations within datasets for researchers and clinical studies. Such data processing allows advancements in the identification of individual pathologies, public health trends, treatment success metrics, and the like. Such output data from the running of these algorithms may be invaluable to individual clinicians, healthcare institutions, and private companies (such as pharmaceutical and biotechnology companies). At the same time, the adoption of clinical AI has been slow. More than 12,000 life-science papers described AI and ML in 2019 alone. Yet the U.S. Food and Drug Administration (FDA) has only approved only slightly more than 30 AWL-based medical technologies to date. Data access is a major barrier to clinical approval. The FDA requires proof that a model works across the entire population. However, privacy protections make it challenging to access enough diverse data to accomplish this goal. Given that there is great value in the operation of secret algorithms on data that also must remain secret, there is a significant need for systems and methods that allow for such zero-trust operations. Such systems and methods enable sensitive data to be analyzed in a secure environment, providing the needed outputs, while maintaining secrecy of both the algorithms involved, as well as the data itself.

Additionally, there is a great need for the identification of patient cohorts that are most suited to be processed by the given algorithm and/or for a researcher's consumption. Rather than randomly seeking partners from a data steward, it is far more efficient to be able to vet a dataset and select only those datasets that are applicable to the given situation. This process is ideally performed in secret by the data steward, without them having access to the criteria of the study (again, to protect the algorithm developer). And even once a dataset is identified, there is a need to ensure that the data is representative, of high quality, and suited for the given purpose it will be applied to. This verification activity is of particular concern if a dataset is being down sampled, or otherwise curated. Lastly, there is great value in being able to have datasets that match a data consumer's given needs identified and recommended when the data is known to be of high quality.

SUMMARY

The present systems and methods relate to the selection, verification and recommending of patient cohorts in a zero-trust environment. Such systems and methods enable improvements in the ability to determine which data stewards have datasets needed by an algorithm developer (or other interested party requiring patient datasets). Such systems enable the selection of datasets without the need to share said data outside of the data steward, as well as enabling validation for the data purchaser and any interested regulatory agency (the FDA for example).

In some embodiments, a dataset selection optimization includes first receiving at data stewards classes of data required by the data consumer. The data stewards process their data (or a subset of their data) into a vector set within a sequestered computing node. These vector sets are transferred to a core management system for minimizing a difference between a target vector and any combination of the data stewards' vector sets. A cost function may also be applied to the vector sets during this optimization.

The minimizing is according to the equation of: Goal=minimize‖T{target}−T(Union({data steward}))‖. Generating the vector set includes encoding the dataset according to the set of classes, generating a matrix of the encoded dataset, wherein each row of the matrix is a patient and each column is a class or subset of classes in the set of classes, and converting the generated matrix into a series of vector spaces. Once the data steward(s) that best match the target vector are identified, they may be placed in contact with the data consumer for access of their information.

Systems and methods are also provided for dataset verification, which includes receiving a sample dataset from a parent dataset. Both datasets are converted into a vector set. Then the distance between the two vector sets are calculated and compared against a threshold. Calculating the difference is by framing the distance as a p-value in a hypothesis test, compared against a different threshold. The sample dataset may be rejected when the calculated difference is above the threshold.

Further, systems and methods are provided for dataset quality quantification. This method also involves the receipt of a sample dataset. A set of rules are leveraged to generate a first score. The set is then converted into a vector set, and this vector set is compared against an example vector set. The example vector set may be generated from an amalgamation of vector sets from different data stewards, or generated from synthetic data. The distance between the two vector sets is calculated, making a second score. The two scores are combined (weighted averages, direct average after normalization, summation, etc.) to yield a final quality score.

Lastly, systems and methods are provided for a way to recommend a data set to a data consumer. This includes A receiving at a set of dataset requirements as a required vector set and querying historical vector sets, which each corresponding to a known dataset. The difference between the required vector set and the known sets is determined, and the known dataset that is closest to the requirements is selected for recommendation.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which.

DETAILED DESCRIPTION

Figure 1A:
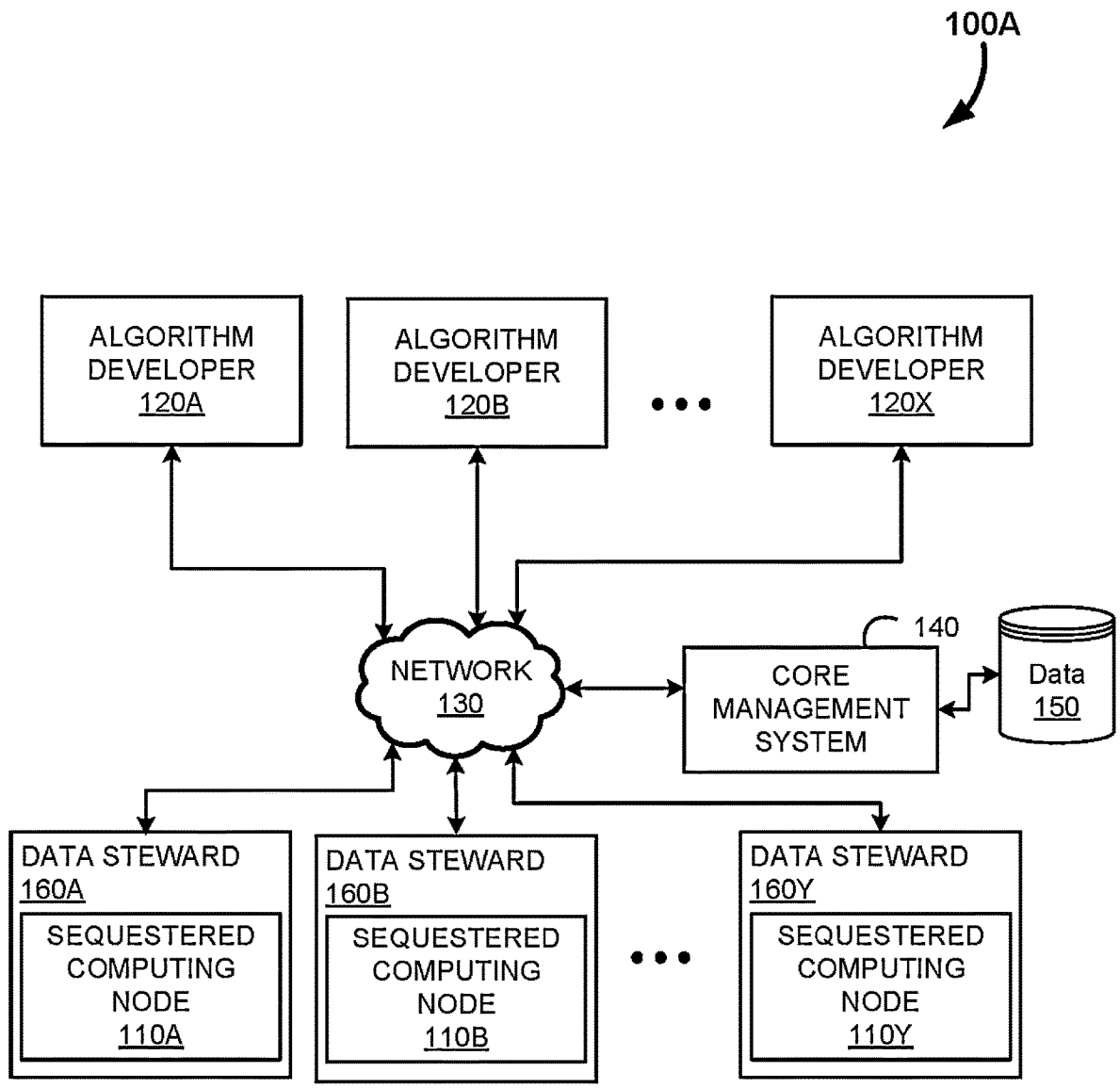
FIGS. 1A and 1B are example block diagrams of a system for zero trust computing of data by an algorithm, in accordance with some embodiment.

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "always," "will," "will not," "shall," "shall not," "must," "must not," "first," "initially," "next," "subsequently," "before," "after," "lastly," and "finally," are not meant to limit the scope of the present invention as the embodiments disclosed herein are merely exemplary.

The present invention relates to systems and methods for the selection, recommendation and verification of sensitive datasets. Such systems and methods may be applied to any given dataset, but may have particular utility within the healthcare setting, where the data is extremely sensitive. As such, the following descriptions will center on healthcare use cases. This particular focus, however, should not artificially limit the scope of the invention. For example, the information processed may include sensitive industry information, payroll or other personally identifiable information, or the like. As such, while much of the disclosure will refer to protected health information (PHI) it should be understood that this may actually refer to any sensitive type of data. Likewise, while the data stewards are generally thought to be a hospital or other healthcare entity, these data stewards may in reality be any entity that has and wishes to process their data.

In some embodiments, the following disclosure will focus upon the term "algorithm". It should be understood that an algorithm may include machine learning (ML) models, neural network models, or other artificial intelligence (AI) models. However, algorithms may also apply to more mundane model types, such as linear models, least mean squares, or any other mathematical functions that convert one or more input values, and results in one or more output models.

Also, in some embodiments of the disclosure, the terms "node", "infrastructure" and "enclave" may be utilized. These terms are intended to be used interchangeably and indicate a computing architecture that is logically distinct (and often physically isolated). In no way does the utilization of one such term limit the scope of the disclosure, and these terms should be read interchangeably. To facilitate discussions, FIG. 1A is an example of a zero-trust infrastructure, shown generally at 100a. This infrastructure includes one or more algorithm developers 120a-x which generate one or more algorithms for processing of data, which in this case is held by one or more data stewards 160a-y. The algorithm developers are generally companies that specialize in data analysis, and are often highly specialized in the types of data that are applicable to their given models/algorithms. However, sometimes the algorithm developers may be individuals, universities, government agencies, or the like. By uncovering powerful insights in vast amounts of information, AI and machine learning (ML) can improve care, increase efficiency, and reduce costs. For example AI analysis of chest x-rays predicted the progression of critical illness in COVID-19. In another example, an image-based deep learning model developed at MIT can predict breast cancer up to five years in advance. And yet another example is an algorithm developed at University of California San Francisco, which can detect pneumothorax (collapsed lung) from CT scans, helping prioritize and treat patients with this life-threatening condition—the first algorithm embedded in a medical device to achieve FDA approval.

Likewise, the data stewards may include public and private hospitals, companies, universities, governmental agencies, or the like. Indeed, virtually any entity with access to sensitive data that is to be analyzed may be a data steward.

The generated algorithms are encrypted at the algorithm developer in whole, or in part, before transmitting to the data stewards, in this example ecosystem. The algorithms are transferred via a core management system 140, which may supplement or transform the data using a localized datastore 150. The core management system also handles routing and deployment of the algorithms. The datastore may also be leveraged for key management in some embodiments that will be discussed in greater detail below.

Each of the algorithm developer 120a-x, and the data stewards 160a-y and the core management system 140 may be coupled together by a network 130. In most cases the network is comprised of a cellular network and/or the internet. However, it is envisioned that the network includes any wide area network (WAN) architecture, including private WAN's, or private local area networks (LANs) in conjunction with private or public WANs.

In this particular system, the data stewards maintain sequestered computing nodes 110a-y which function to actually perform the computation of the algorithm on the dataset. The sequestered computing nodes, or "enclaves", may be physically separate computer server systems, or may encompass virtual machines operating within a greater network of the data steward's systems. The sequestered computing nodes should be thought of as a vault. The encrypted algorithm and encrypted datasets are supplied to the vault, which is then sealed. Encryption keys 390 unique to the vault are then provided, which allows the decryption of the data and models to occur. No party has access to the vault at this time, and the algorithm is able to securely operate on the data. The data and algorithms may then be destroyed, or maintained as encrypted, when the vault is "opened" in order to access the report/output derived from the application of the algorithm on the dataset. Due to the specific sequestered computing node being required to decrypt the given algorithm(s) and data, there is no way they can be intercepted and decrypted. This system relies upon public-private key techniques, where the algorithm developer utilizes the public key 390 for encryption of the algorithm, and the sequestered computing node includes the private key in order to perform the decryption. In some embodiments, the private key may be hardware (in the case of Azure, for example) or software linked (in the case of AWS, for example).

In some particular embodiments, the system sends algorithm models via an Azure Confidential Computing environment to two data steward environments. Upon verification, the model and the data entered the Intel SGX sequestered enclave where the model is able to be validated against the PHI data sets. Throughout the process, the algorithm owner cannot see the data, the data steward cannot see the algorithm model, and the management core can see neither the data nor the model.

The data steward uploads encrypted data to their cloud environment using an encrypted connection that terminates inside an Intel SGX-sequestered enclave. Then, the algorithm developer submits an encrypted, containerized AI model which also terminates into an Intel SGX-sequestered enclave. A key management system in the management core enables the containers to authenticate and then run the model on the data within the enclave. The data steward never sees the algorithm inside the container and the data is never visible to the algorithm developer. Neither component leaves the enclave. After the model runs, the developer receives a performance report on the values of the algorithm's performance along with a summary of the data characteristics. Finally, the algorithm owner may request that an encrypted artifact containing information about validation results is stored for regulatory compliance purposes and the data and the algorithm are wiped from the system.

Figure 1B:
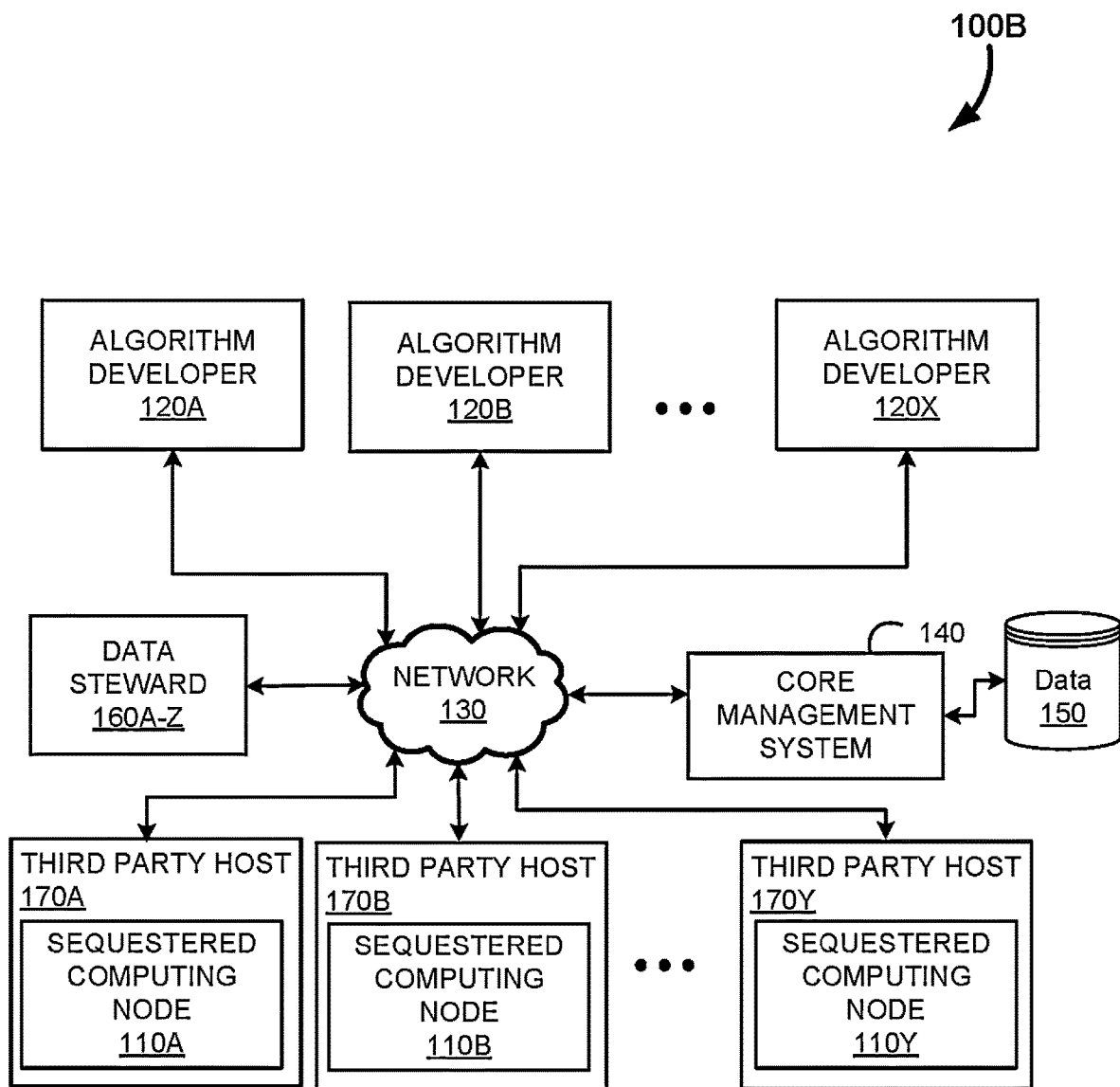

FIG. 1B provides a similar ecosystem 100b. This ecosystem also includes one or more algorithm developers 120a-x, which generate, encrypt and output their models. The core management system 140 receives these encrypted payloads, and in some embodiments, transforms or augments unencrypted portions of the payloads. The major difference between this substantiation and the prior figure, is that the sequestered computing node(s) 110a-y are present within a third party host 170a-y. An example of a third-party host may include an offsite server such as Amazon Web Service (AWS) or similar cloud infrastructure. In such situations, the data steward encrypts their dataset(s) and provides them, via the network, to the third party hosted sequestered computing node(s) 110a-y. The output of the algorithm running on the dataset is then transferred from the sequestered computing node in the third-party, back via the network to the data steward (or potentially some other recipient).

In some specific embodiments, the system relies on a unique combination of software and hardware available through Azure Confidential Computing. The solution uses virtual machines (VMs) running on specialized Intel processors with Intel Software Guard Extension (SGX), in this embodiment, running in the third party system. Intel SGX creates sequestered portions of the hardware's processor and memory known as "enclaves" making it impossible to view data or code inside the enclave. Software within the management core handles encryption, key management, and workflows.

In some embodiments, the system may be some hybrid between FIGS. 1A and 1B. For example, some datasets may be processed at local sequestered computing nodes, especially extremely large datasets, and others may be processed at third parties. Such systems provide flexibility based upon computational infrastructure, while still ensuring all data and algorithms remain sequestered and not visible except to their respective owners.

Figure 2A:
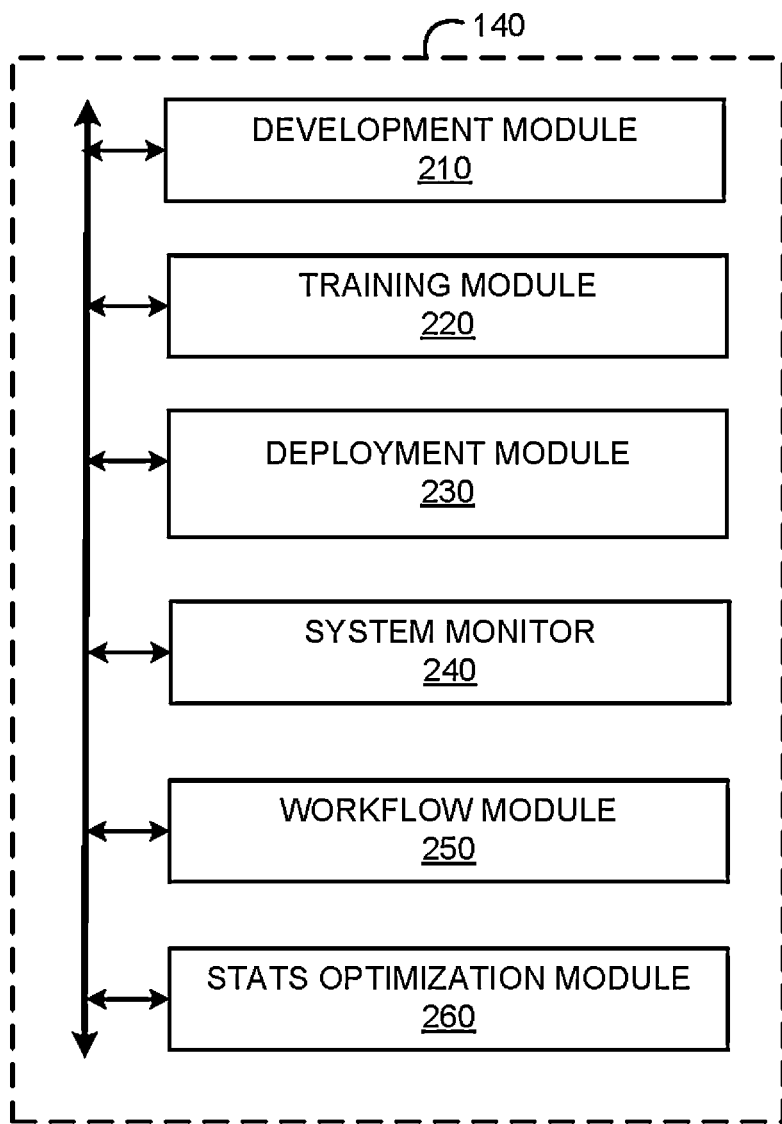
FIG. 2A is an example block diagram showing the core management system, in accordance with some embodiment.

Turning now to FIG. 2A, greater detail is provided regarding the core management system 140. The core management system 140 may include a data science development module 210, a data harmonizer workflow creation module 250, a software deployment module 230, a federated master algorithm training module 220, a system monitoring module 240, and a statistical optimization module 260.

The data science development module 210 may be configured to receive input data requirements from the one or more algorithm developers for the optimization and/or validation of the one or more models. The input data requirements define the objective for data curation, data transformation, and data harmonization workflows. The input data requirements also provide constraints for identifying data assets acceptable for use with the one or more models. The data harmonizer workflow creation module 250 may be configured to manage transformation, harmonization, and annotation protocol development and deployment. The software deployment module 230 may be configured along with the data science development module 210 and the data harmonizer workflow creation module 250 to assess data assets for use with one or more models. This process can be automated or can be an interactive search/query process. The software deployment module 230 may be further configured along with the data science development module 210 to integrate the models into a sequestered capsule computing framework, along with required libraries and resources.

The statistical optimization module 260 may consume statistical data from data stewards regarding their data sets (known a "metastats"). These metastats are generally vectors of the given datasets after an encoding event. The encoding is determined based upon the needs of a data consumer. These metastats are used by the stats optimization module 260 to select from between various data sources, the cohorts that best meet a given set of requirements by the data consumer (the algorithm developer or other data user). In some embodiments, this optimization subtracts the given set of vectors for the dataset, in combinations with other dataset vectors, against a desired set of vectors determines which sets/cohorts together best meet the requirements of the data consumer. Significant detail into this cohort selection process will be discussed below.

In some embodiments, it is desired to develop a robust, superior algorithm/model that has learned from multiple disjoint private data sets (e.g., clinical and health data) collected by data hosts from sources (e.g., patients). The federated master algorithm training module may be configured to aggregate the learning from the disjoint data sets into a single master algorithm. In different embodiments, the algorithmic methodology for the federated training may be different. For example, sharing of model parameters, ensemble learning, parent-teacher learning on shared data and many other methods may be developed to allow for federated training. The privacy and security requirements, along with commercial considerations such as the determination of how much each data system might be paid for access to data, may determine which federated training methodology is used.

The system monitoring module 240 monitors activity in sequestered computing nodes. Monitored activity can range from operational tracking such as computing workload, error state, and connection status as examples to data science monitoring such as amount of data processed, algorithm convergence status, variations in data characteristics, data errors, algorithm/model performance metrics, and a host of additional metrics, as required by each use case and embodiment.

In some instances, it is desirable to augment private data sets with additional data located at the core management system (join data 150). For example, geolocation air quality data could be joined with geolocation data of patients to ascertain environmental exposures. In certain instances, join data may be transmitted to sequestered computing nodes to be joined with their proprietary datasets during data harmonization or computation.

The sequestered computing nodes may include a harmonizer workflow module, harmonized data, a runtime server, a system monitoring module, and a data management module (not shown). The transformation, harmonization, and annotation workflows managed by the data harmonizer workflow creation module may be deployed by and performed in the environment by harmonizer workflow module using transformations and harmonized data. In some instances, the join data may be transmitted to the harmonizer workflow module to be joined with data during data harmonization. The runtime server may be configured to run the private data sets through the algorithm/model.

The system monitoring module monitors activity in the sequestered computing node. Monitored activity may include operational tracking such as algorithm/model intake, workflow configuration, and data host onboarding, as required by each use case and embodiment. The data management module may be configured to import data assets such as private data sets while maintaining the data assets within the pre-exiting infrastructure of the data stewards.

Figure 2B:
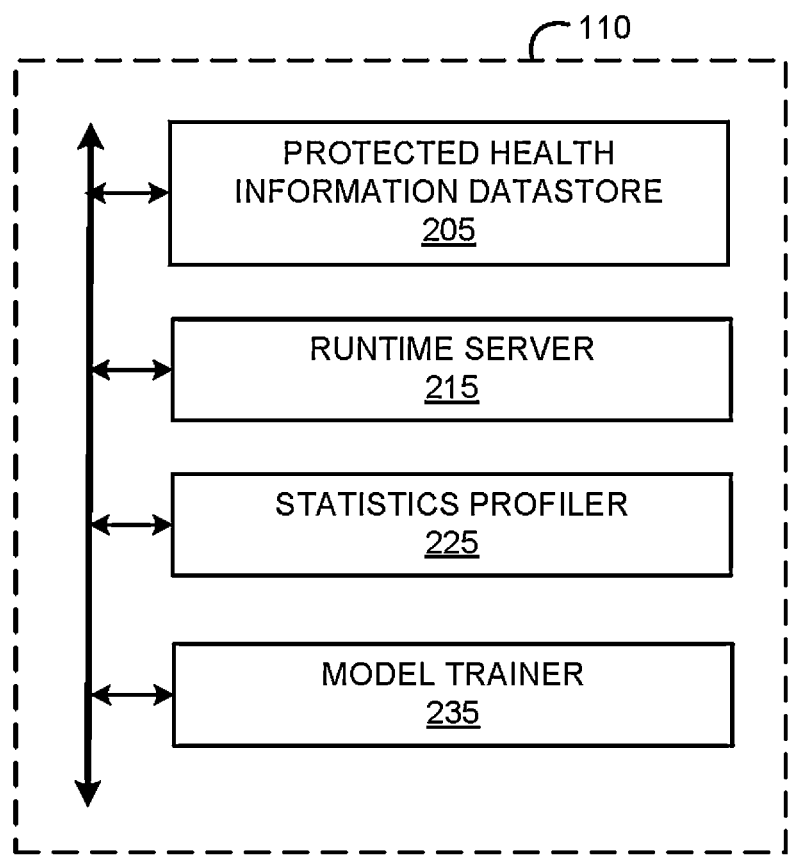
FIG. 2B is an example block diagram showing the sequestered computing node, in accordance with some embodiment.

FIG. 2B provides a more detailed illustration of the contents of the sequestered computing node 110. In this example embodiment, the computing node includes a database of the protected health information 205 that is being either operated upon or selected for utilization by another data consumer. A runtime server 215 is the computing element that consumes an algorithm and applies it against the PHI 205. The runtime server 215 likewise executes the model trainer 235 to train a given algorithm on the PHI 205. A statistical profiler 225 is likewise executed using the runtime server 215 to characterize the PHI 205 (or some subset of the data in the database) to generate metastats. These metastats are then leveraged by the core management system 140 to select which data, from which data stewards 160 to suggest to the data consumer. The data consumer (algo developer, researcher, clinical trial manager, etc.) may then contract with the appropriate data stewards 160 to get access to the data directly.

Figure 3:
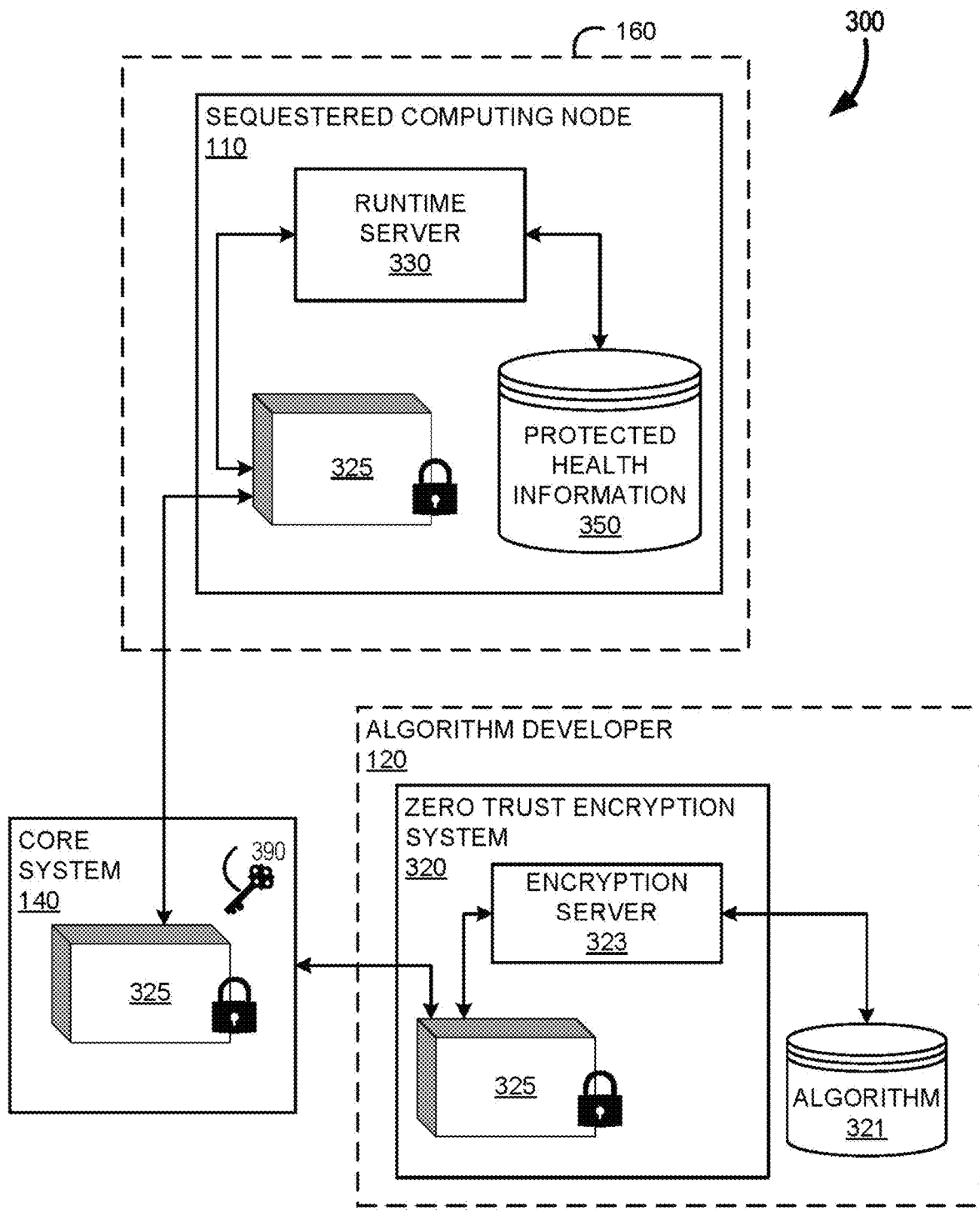
FIG. 3 is an example block diagram showing a first model for the zero-trust data flow, in accordance with some embodiment.

Turning now to FIG. 3, a first model of the flow of algorithms and data are provided, generally at 300. The Zero-Trust Encryption System 320 manages the encryption, by an encryption server 323, of all the algorithm developer's 120 software assets 321 in such a way as to prevent exposure of intellectual property (including source or object code) to any outside party, including the entity running the core management system 140 and any affiliates, during storage, transmission and runtime of said encrypted algorithms 325. In this embodiment, the algorithm developer is responsible for encrypting the entire payload 325 of the software using its own encryption keys. Decryption is only ever allowed at runtime in a sequestered capsule computing environment 110.

The core management system 140 receives the encrypted computing assets (algorithms) 325 from the algorithm developer 120. Decryption keys to these assets are not made available to the core management system 140 so that sensitive materials are never visible to it. The core management system 140 distributes these assets 325 to a multitude of data steward nodes 160 where they can be processed further, in combination with private datasets, such as protected health information (PHI) 350.

Each Data Steward Node 160 maintains a sequestered computing node 110 that is responsible for allowing the algorithm developer's encrypted software assets 325 to compute on a local private dataset 350 that is initially encrypted. Within data steward node 160, one or more local private datasets (not illustrated) is harmonized, transformed, and/or annotated and then this dataset is encrypted by the data steward, into a local dataset 350, for use inside the sequestered computing node 110.

The sequestered computing node 110 receives the encrypted software assets 325 and encrypted data steward dataset(s) 350 and manages their decryption in a way that prevents visibility to any data or code at runtime at the runtime server 330. In different embodiments this can be performed using a variety of secure computing enclave technologies, including but not limited to hardware-based and software-based isolation.

In this present embodiment, the entire algorithm developer software asset payload 325 is encrypted in a way that it can only be decrypted in an approved sequestered computing enclave/node 110. This approach works for sequestered enclave technologies that do not require modification of source code or runtime environments in order to secure the computing space (e.g., software-based secure computing enclaves).

Figure 4:
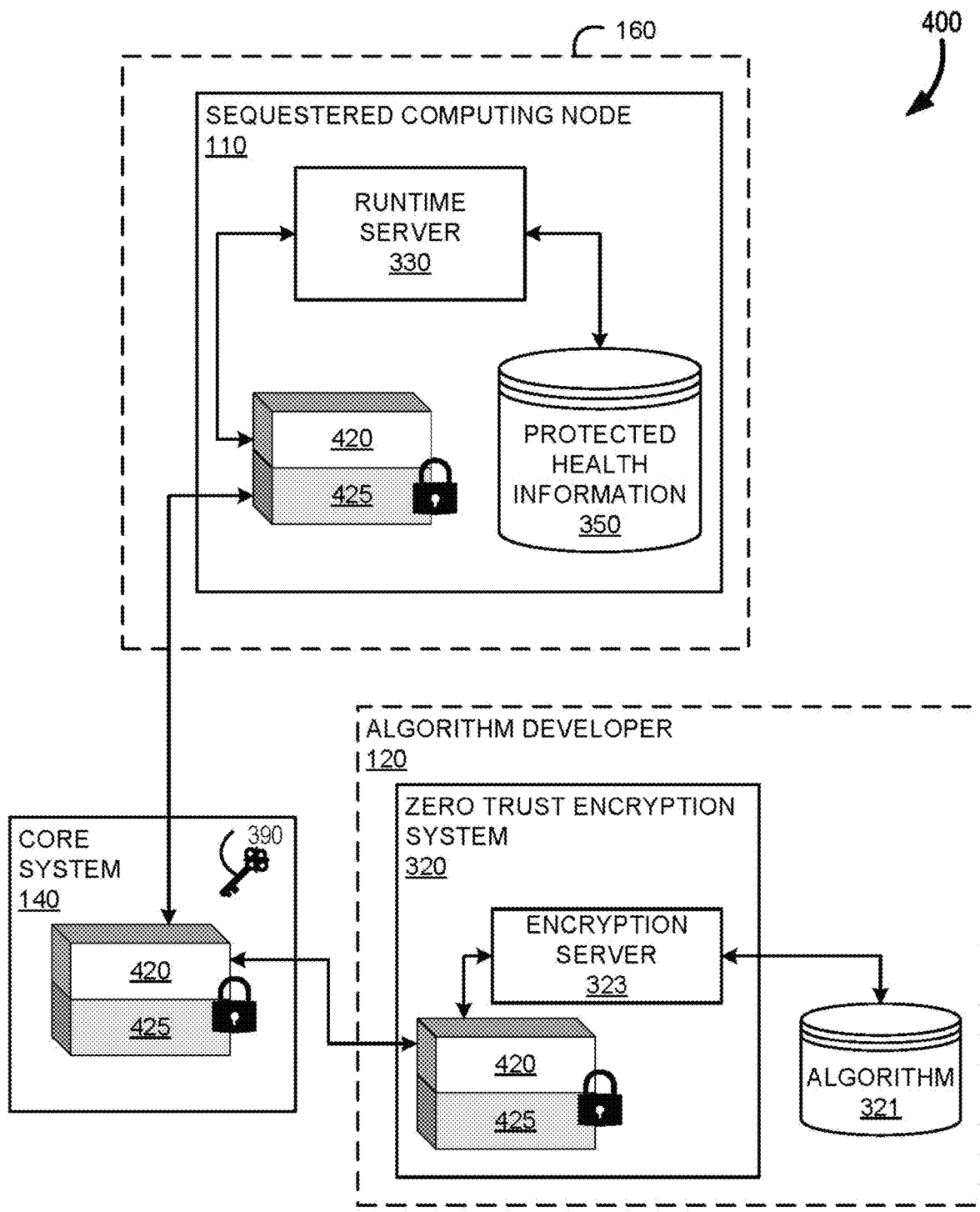
FIG. 4 is an example block diagram showing a second model for the zero-trust data flow, in accordance with some embodiment.

Turning to FIG. 4, the general environment is maintained, as seen generally at 400, however in this embodiment, the encryption server 323 takes the algorithm asset 321, and only encrypts a specific sensitive layer 425 (generally comprising the algorithm weights), while leaving remaining non-sensitive algorithm elements 420 (such as the container and base model minus weights) unencrypted. This embodiment has the advantage of allowing the unencrypted portion 420 of the payload to be transformed, or otherwise altered, by either the core management system 140, or by the data steward 160. An example would be the conversion of specific library dependencies from the original operating system to Enclave OS, a special operating system that runs code in an Intel SGX sequestered computing enclave.

Figure 5:
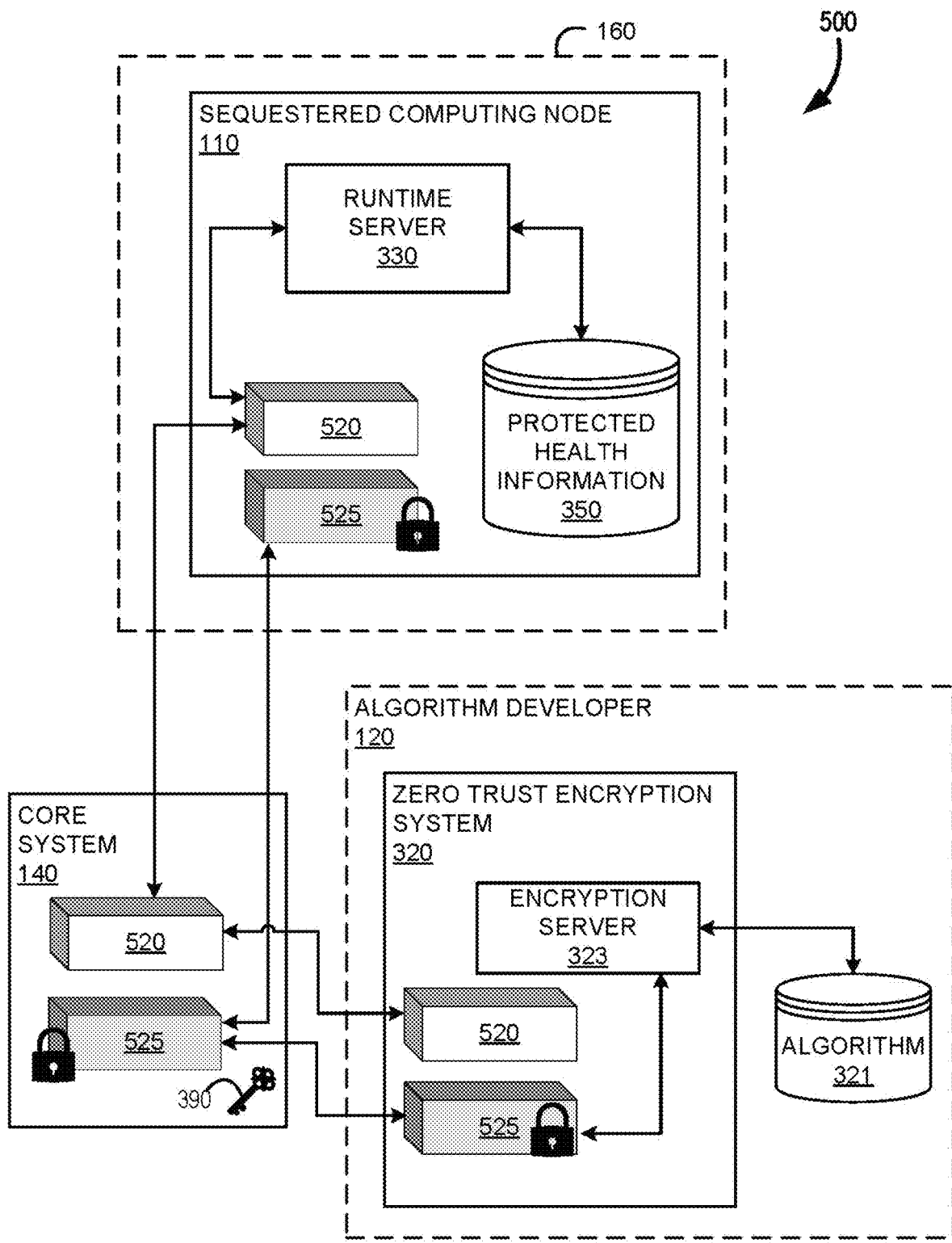
FIG. 5 is an example block diagram showing a third model for the zero-trust data flow, in accordance with some embodiment.

In a similar manner, FIG. 5 provides an example embodiment of a system whereby the sensitive and non-sensitive portions of the developer assets 321 are treated differently, seen generally at 500. In this example, however, rather than only encrypting a specific layer of the ultimate payload, the assets are separated into two portions: the sensitive elements 525 and the non-sensitive elements 520. The non-sensitive elements 520, are then transferred in the clear, while the sensitive elements 525 are encrypted before leaving the zero trust encryption system 320. As with the embodiment found in FIG. 4, this methodology of splitting the payload into two entirely separate elements allows the unencrypted non-sensitive payload 520 to be modified.

Figure 6:
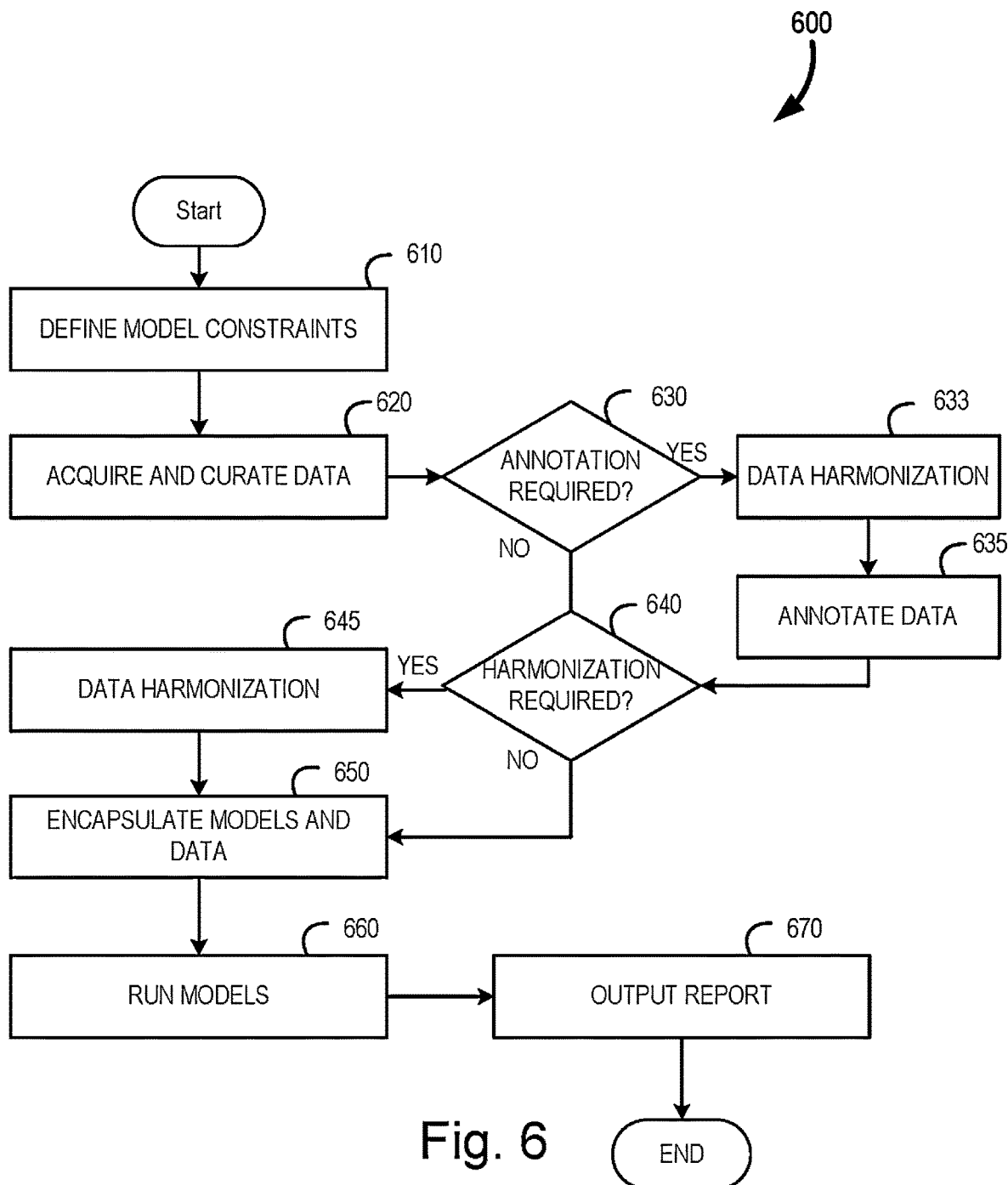
FIG. 6 is a flowchart for an example process for the operation of the zero-trust data processing system, in accordance with some embodiment.

Turning to FIG. 6, one embodiment of the process for deployment and running of algorithms within the sequestered computing nodes is illustrated, at 600. Initially the algorithm developer provides the algorithm to the system. The at least one algorithm/model is generated by the algorithm developer using their own development environment, tools, and seed data sets (e.g., training/testing data sets). In some embodiments, the algorithms may be trained on external datasets instead, as will be discussed further below. The algorithm developer provides constraints (at 610) for the optimization and/or validation of the algorithm(s). Constraints may include any of the following: (i) training constraints, (ii) data preparation constraints, and (iii) validation constraints. These constraints define objectives for the optimization and/or validation of the algorithm(s) including data preparation (e.g., data curation, data transformation, data harmonization, and data annotation), model training, model validation, and reporting.

In some embodiments, the training constraints may include, but are not limited to, at least one of the following: hyperparameters, regularization criteria, convergence criteria, algorithm termination criteria, training/validation/test data splits defined for use in algorithm(s), and training/testing report requirements. A model hyper parameter is a configuration that is external to the model, and which value cannot be estimated from data. The hyperparameters are settings that may be tuned or optimized to control the behavior of a ML or AI algorithm and help estimate or learn model parameters.

Regularization constrains the coefficient estimates towards zero. This discourages the learning of a more complex model in order to avoid the risk of overfitting. Regularization, significantly reduces the variance of the model, without a substantial increase in its bias. The convergence criterion is used to verify the convergence of a sequence (e.g., the convergence of one or more weights after a number of iterations). The algorithm termination criteria define parameters to determine whether a model has achieved sufficient training. Because algorithm training is an iterative optimization process, the training algorithm may perform the following steps multiple times. In general, termination criteria may include performance objectives for the algorithm, typically defined as a minimum amount of performance improvement per iteration or set of iterations.

The training/testing report may include criteria that the algorithm developer has an interest in observing from the training, optimization, and/or testing of the one or more models. In some instances, the constraints for the metrics and criteria are selected to illustrate the performance of the models. For example, the metrics and criteria such as mean percentage error may provide information on bias, variance, and other errors that may occur when finalizing a model such as vanishing or exploding gradients. Bias is an error in the learning algorithm. When there is high bias, the learning algorithm is unable to learn relevant details in the data. Variance is an error in the learning algorithm, when the learning algorithm tries to over-learn from the dataset or tries to fit the training data as closely as possible. Further, common error metrics such as mean percentage error and R2 score are not always indicative of accuracy of a model, and thus the algorithm developer may want to define additional metrics and criteria for a more in depth look at accuracy of the model.

Figure 7A:
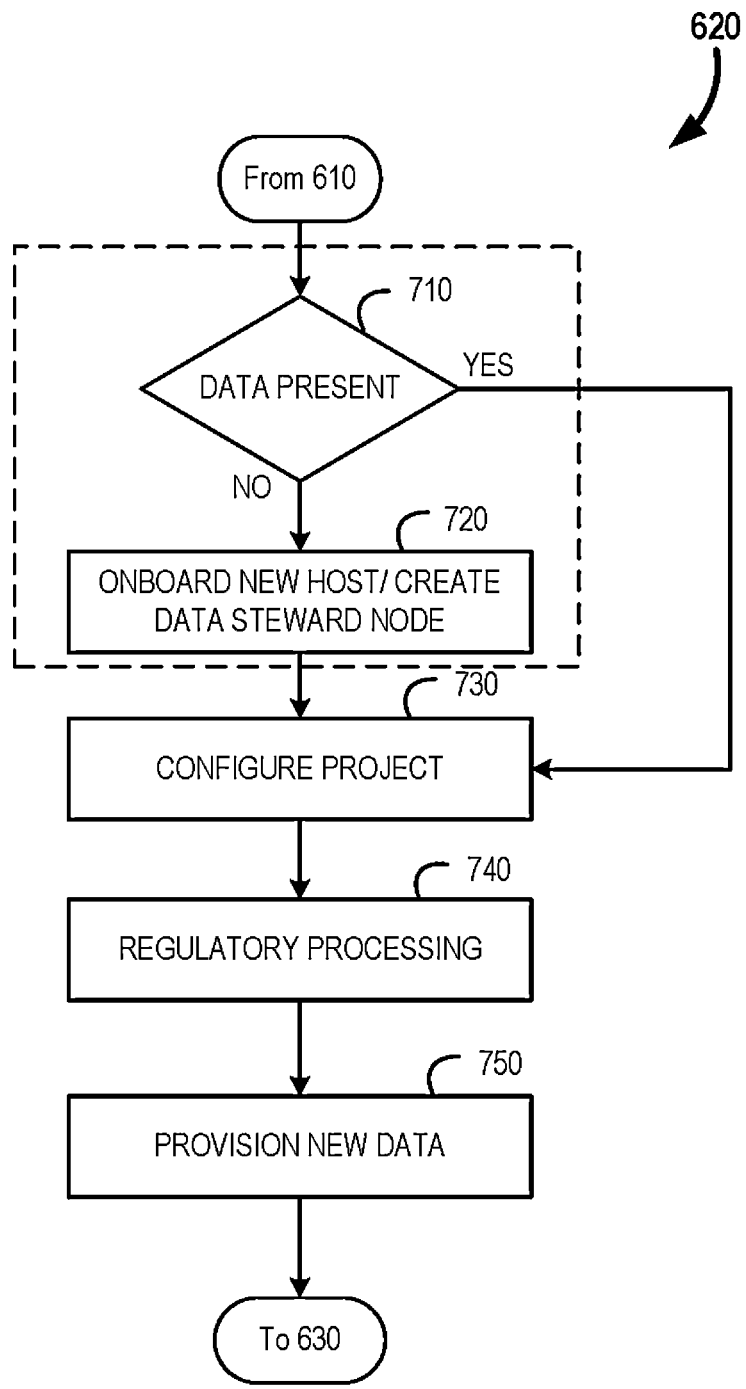
FIG. 7A a flowchart for an example process of acquiring and curating data, in accordance with some embodiment.

Next, data assets that will be subjected to the algorithm(s) are identified, acquired, and curated (at 620). FIG. 7A provides greater detail of this acquisition and curation of the data. Often, the data may include healthcare related data (PHI). Initially, there is a query if data is present (at 710). The identification process may be performed automatically by the platform running the queries for data assets (e.g., running queries on the provisioned data stores using the data indices) using the input data requirements as the search terms and/or filters. Alternatively, this process may be performed using an interactive process, for example, the algorithm developer may provide search terms and/or filters to the platform. The platform may formulate questions to obtain additional information, the algorithm developer may provide the additional information, and the platform may run queries for the data assets (e.g., running queries on databases of the one or more data hosts or web crawling to identify data hosts that may have data assets) using the search terms, filters, and/or additional information. In either instance, the identifying is performed using differential privacy for sharing information within the data assets by describing patterns of groups within the data assets while withholding private information about individuals in the data assets.

Figure 7B:
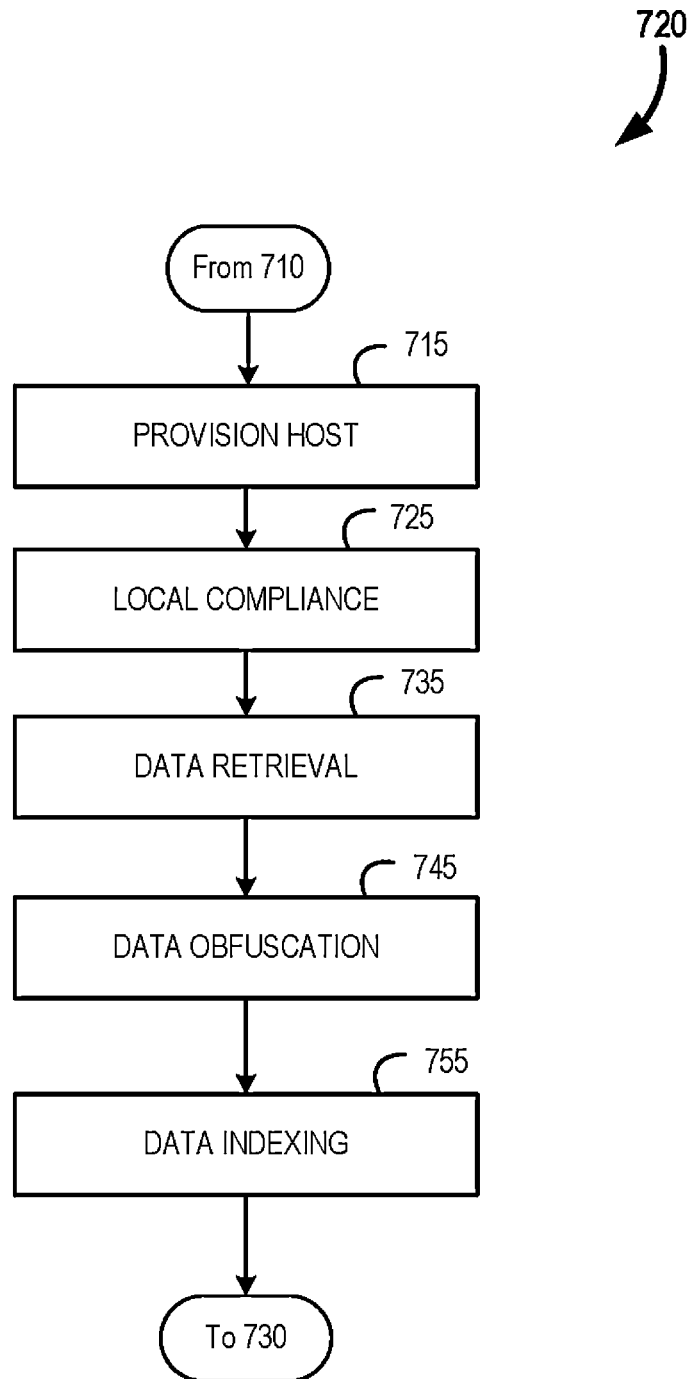
FIG. 7B a flowchart for an example process of onboarding a new host data steward, in accordance with some embodiment.

If the assets are not available, the process generates a new data steward node (at 720). The data query and onboarding activity (surrounded by a dotted line) is illustrated in this process flow of acquiring the data; however, it should be realized that these steps may be performed anytime prior to model and data encapsulation (step 650 in FIG. 6). Onboarding/creation of a new data steward node is shown in greater detail in relation to FIG. 7B. In this example process a data host compute and storage infrastructure (e.g., a sequestered computing node as described with respect to FIGS. 1A-5) is provisioned (at 715) within the infrastructure of the data steward. In some instances, the provisioning includes deployment of encapsulated algorithms in the infrastructure, deployment of a physical computing device with appropriately provisioned hardware and software in the infrastructure, deployment of storage (physical data stores or cloud-based storage), or deployment on public or private cloud infrastructure accessible via the infrastructure, etc.

Next, governance and compliance requirements are performed (at 725). In some instances, the governance and compliance requirements includes getting clearance from an institutional review board, and/or review and approval of compliance of any project being performed by the platform and/or the platform itself under governing law such as the Health Insurance Portability and Accountability Act (HIPAA). Subsequently, the data assets that the data steward desires to be made available for optimization and/or validation of algorithm(s) are retrieved (at 735). In some instances, the data assets may be transferred from existing storage locations and formats to provisioned storage (physical data stores or cloud-based storage) for use by the sequestered computing node (curated into one or more data stores). The data assets may then be obfuscated (at 745). Data obfuscation is a process that includes data encryption or tokenization, as discussed in much greater detail below. Lastly, the data assets may be indexed (at 755). Data indexing allows queries to retrieve data from a database in an efficient manner. The indexes may be related to specific tables and may be comprised of one or more keys or values to be looked up in the index (e.g., the keys may be based on a data table's columns or rows).

Returning to FIG. 7A, after the creation of the new data steward, the project may be configured (at 730). In some instances, the data steward computer and storage infrastructure is configured to handle a new project with the identified data assets. In some instances, the configuration is performed similarly to the process described of FIG. 7B. Next, regulatory approvals (e.g., IRB and other data governance processes) are completed and documented (at 740). Lastly, the new data is provisioned (at 750). In some instances, the data storage provisioning includes identification and provisioning of a new logical data storage location, along with creation of an appropriate data storage and query structure.

Returning now to FIG. 6, after the data is acquired and configured, a query is performed if there is a need for data annotation (at 630). If so, the data is initially harmonized (at 633) and then annotated (at 635). Data harmonization is the process of collecting data sets of differing file formats, naming conventions, and columns, and transforming it into a cohesive data set. The annotation is performed by the data steward in the sequestered computing node. A key principle to the transformation and annotation processes is that the platform facilitates a variety of processes to apply and refine data cleaning and transformation algorithms, while preserving the privacy of the data assets, all without requiring data to be moved outside of the technical purview of the data steward.

Figure 8:
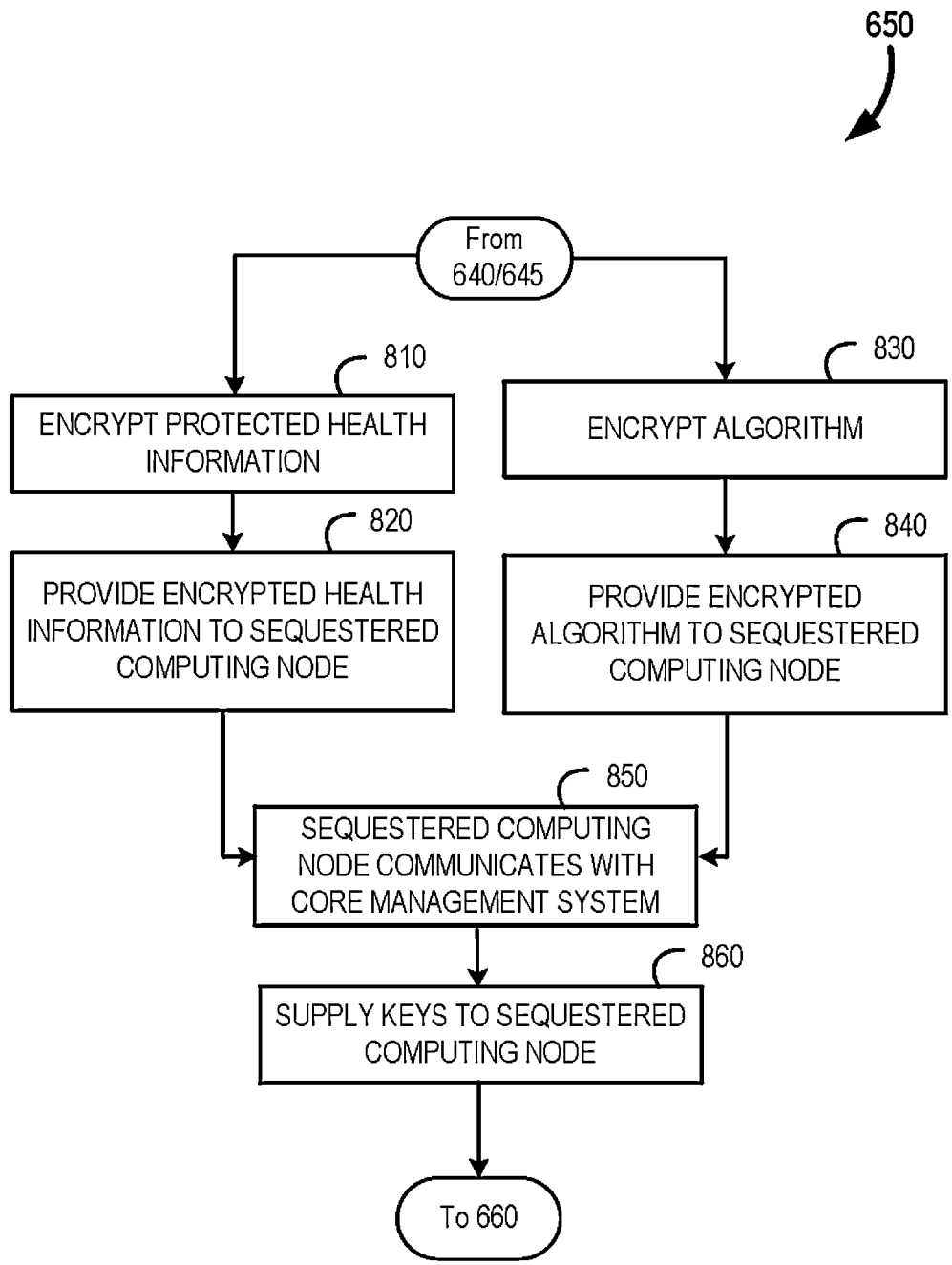
FIG. 8 is a flowchart for an example process of encapsulating the algorithm and data, in accordance with some embodiment.

After annotation, or if annotation was not required, another query determines if additional data harmonization is needed (at 640). If so, then there is another harmonization step (at 645) that occurs in a manner similar to that disclosed above. After harmonization, or if harmonization isn't needed, the models and data are encapsulated (at 650). Data and model encapsulation is described in greater detail in relation to FIG. 8. In the encapsulation process the protected data, and the algorithm are each encrypted (at 810 and 830 respectively). In some embodiments, the data is encrypted either using traditional encryption algorithms (e.g., RSA) or homomorphic encryption.

Next the encrypted data and encrypted algorithm are provided to the sequestered computing node (at 820 and 840 respectively). There processes of encryption and providing the encrypted payloads to the sequestered computing nodes may be performed asynchronously, or in parallel. Subsequently, the sequestered computing node may phone home to the core management node (at 850) requesting the keys needed. These keys are then also supplied to the sequestered computing node (at 860), thereby allowing the decryption of the assets.

Returning again to FIG. 6, once the assets are all within the sequestered computing node, they may be decrypted and the algorithm may run against the dataset (at 660). The results from such runtime may be outputted as a report (at 670) for downstream consumption.

Figure 9:
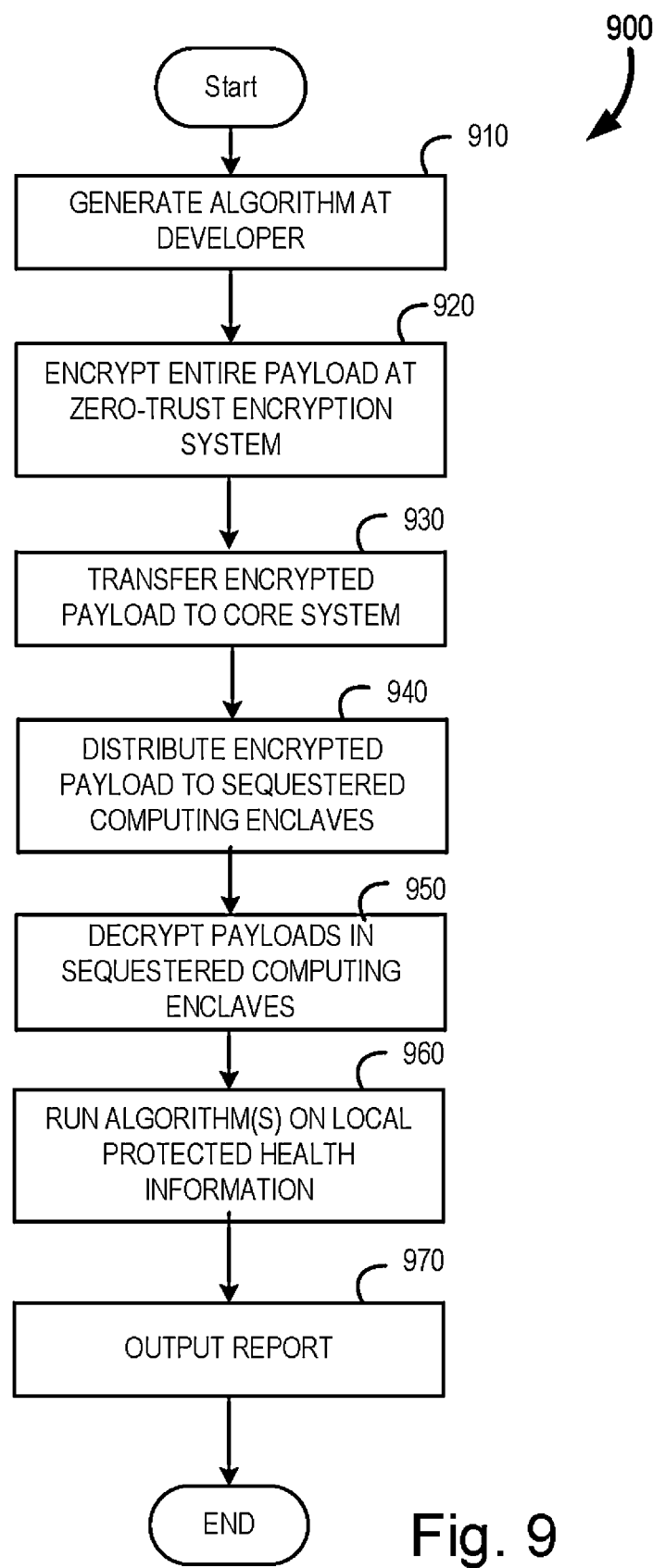
FIG. 9 is a flowchart for an example process of a first model of algorithm encryption and handling, in accordance with some embodiment.

Turning now to FIG. 9, a first embodiment of the system for zero-trust processing of the data assets by the algorithm is provided, at 900. In this example process, the algorithm is initially generated by the algorithm developer (at 910) in a manner similar to that described previously. The entire algorithm, including its container, is then encrypted (at 920), using a public key, by the encryption server within the zero-trust system of the algorithm developer's infrastructure. The entire encrypted payload is provided to the core management system (at 930). The core management system then distributes the encrypted payload to the sequestered computing enclaves (at 940).

Likewise, the data steward collects the data assets desired for processing by the algorithm. This data is also provided to the sequestered computing node. In some embodiments, this data may also be encrypted. The sequestered computing node then contacts the core management system for the keys. The system relies upon public-private key methodologies for the decryption of the algorithm, and possibly the data (at 950).

After decryption within the sequestered computing node, the algorithm(s) are run (at 960) against the protected health information (or other sensitive information based upon the given use case). The results are then output (at 970) to the appropriate downstream audience (generally the data steward, but may include public health agencies or other interested parties).

Figure 10:
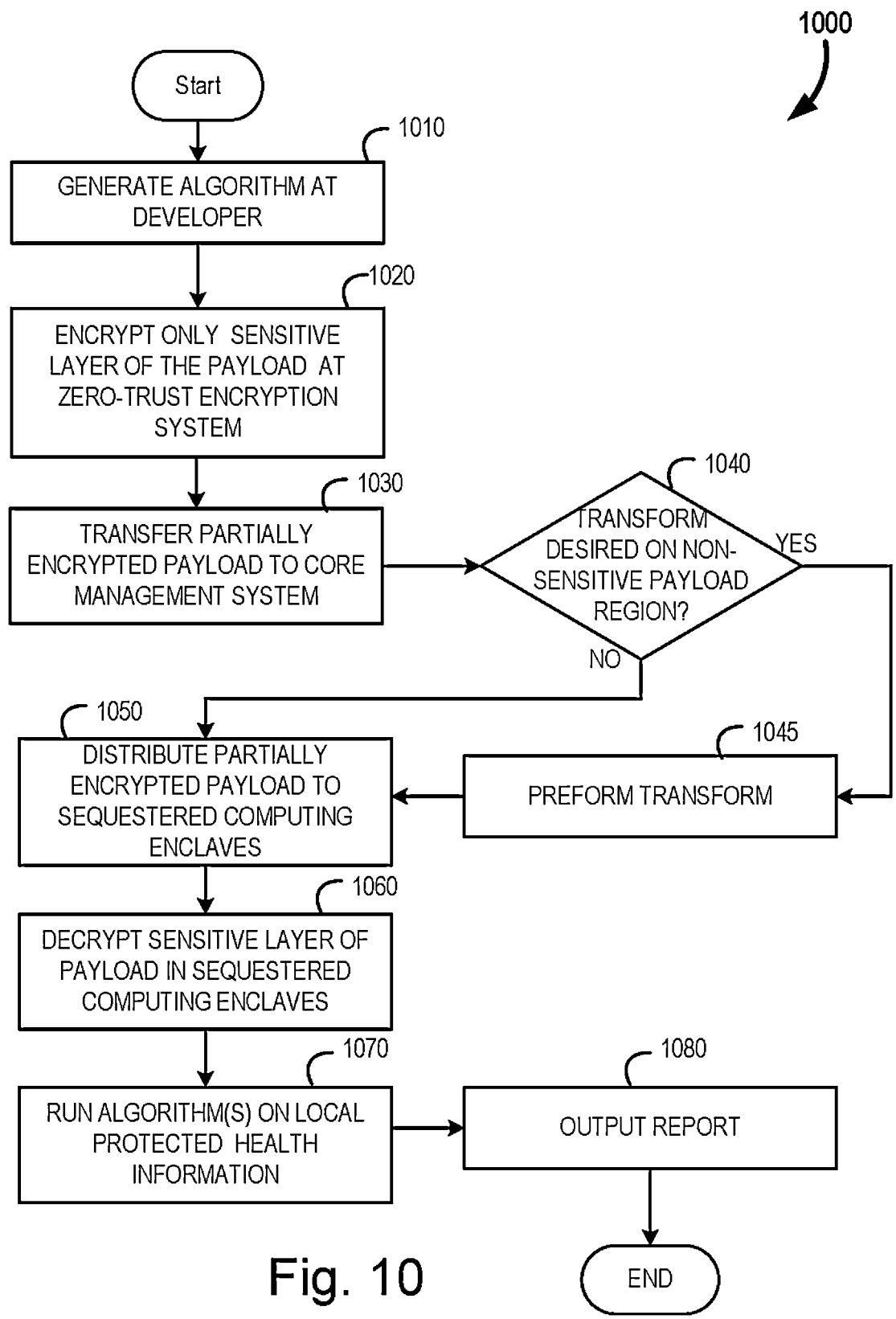
FIG. 10 is a flowchart for an example process of a second model of algorithm encryption and handling, in accordance with some embodiments.

FIG. 10, on the other hand, provides another methodology of zero-trust computation that has the advantage of allowing some transformation of the algorithm data by either the core management system or the data steward themselves, shown generally at 1000. As with the prior embodiment, the algorithm is initially generated by the algorithm developer (at 1010). However, at this point the two methodologies diverge. Rather than encrypt the entire algorithm payload, it differentiates between the sensitive portions of the algorithm (generally the algorithm weights), and non-sensitive portions of the algorithm (including the container, for example). The process then encrypts only layers of the payload that have been flagged as sensitive (at 1020).

The partially encrypted payload is then transferred to the core management system (at 1030). At this stage a determination is made whether a modification is desired to the non-sensitive, non-encrypted portion of the payload (at 1040). If a modification is desired, then it may be performed in a similar manner as discussed previously (at 1045).

If no modification is desired, or after the modification is performed, the payload may be transferred (at 1050) to the sequestered computing node located within the data steward infrastructure (or a third party). Although not illustrated, there is again an opportunity at this stage to modify any non-encrypted portions of the payload when the algorithm payload is in the data steward's possession.

Next, the keys unique to the sequestered computing node are employed to decrypt the sensitive layer of the payload (at 1060), and the algorithms are run against the locally available protected health information (at 1070). In the use case where a third party is hosting the sequestered computing node, the protected health information may be encrypted at the data steward before being transferred to the sequestered computing node at said third party. Regardless of sequestered computing node location, after runtime, the resulting report is outputted to the data steward and/or other interested party (at 1080).

Figure 11:
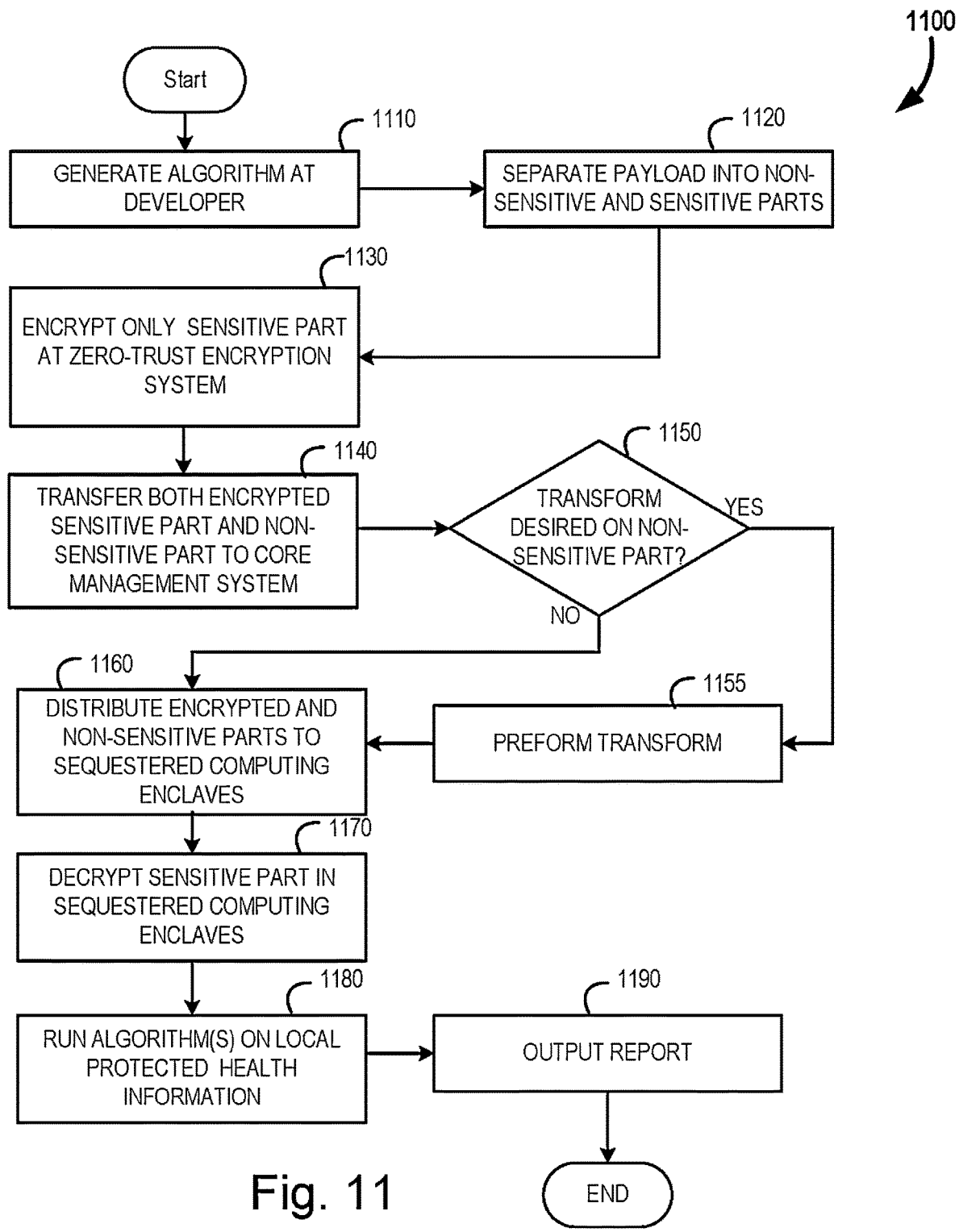
FIG. 11 is a flowchart for an example process of a third model of algorithm encryption and handling, in accordance with some embodiments.

FIG. 11, as seen at 1100, is similar to the prior two figures in many regards. The algorithm is similarly generated at the algorithm developer (at 1110); however, rather than being subject to an encryption step immediately, the algorithm payload may be logically separated into a sensitive portion and a non-sensitive portion (at 1120). To ensure that the algorithm runs properly when it is ultimately decrypted in the (sequestered) sequestered computing enclave, instructions about the order in which computation steps are carried out may be added to the unencrypted portion of the payload.

Subsequently, the sensitive portion is encrypted at the zero-trust encryption system (at 1130), leaving the non-sensitive portion in the clear. Both the encrypted portion and the non-encrypted portion of the payload are transferred to the core management system (at 1140). This transfer may be performed as a single payload, or may be done asynchronously. Again, there is an opportunity at the core management system to perform a modification of the non-sensitive portion of the payload. A query is made if such a modification is desired (at 1150), and if so it is performed (at 1155). Transformations may be similar to those detailed above.

Subsequently, the payload is provided to the sequestered computing node(s) by the core management system (at 1160). Again, as the payload enters the data steward node(s), it is possible to perform modifications to the non-encrypted portion(s). Once in the sequestered computing node, the sensitive portion is decrypted (at 1170), the entire algorithm payload is run (at 1180) against the data that has been provided to the sequestered computing node (either locally or supplied as an encrypted data package). Lastly, the resulting report is outputted to the relevant entities (at 1190).

Any of the above modalities of operation provide the instant zero-trust architecture with the ability to process a data source with an algorithm without the ability for the algorithm developer to have access to the data being processed, the data steward being unable to view the algorithm being used, or the core management system from having access to either the data or the algorithm. This uniquely provides each party the peace of mind that their respective valuable assets are not at risk, and facilitates the ability to easily, and securely, process datasets.

Figure 12:
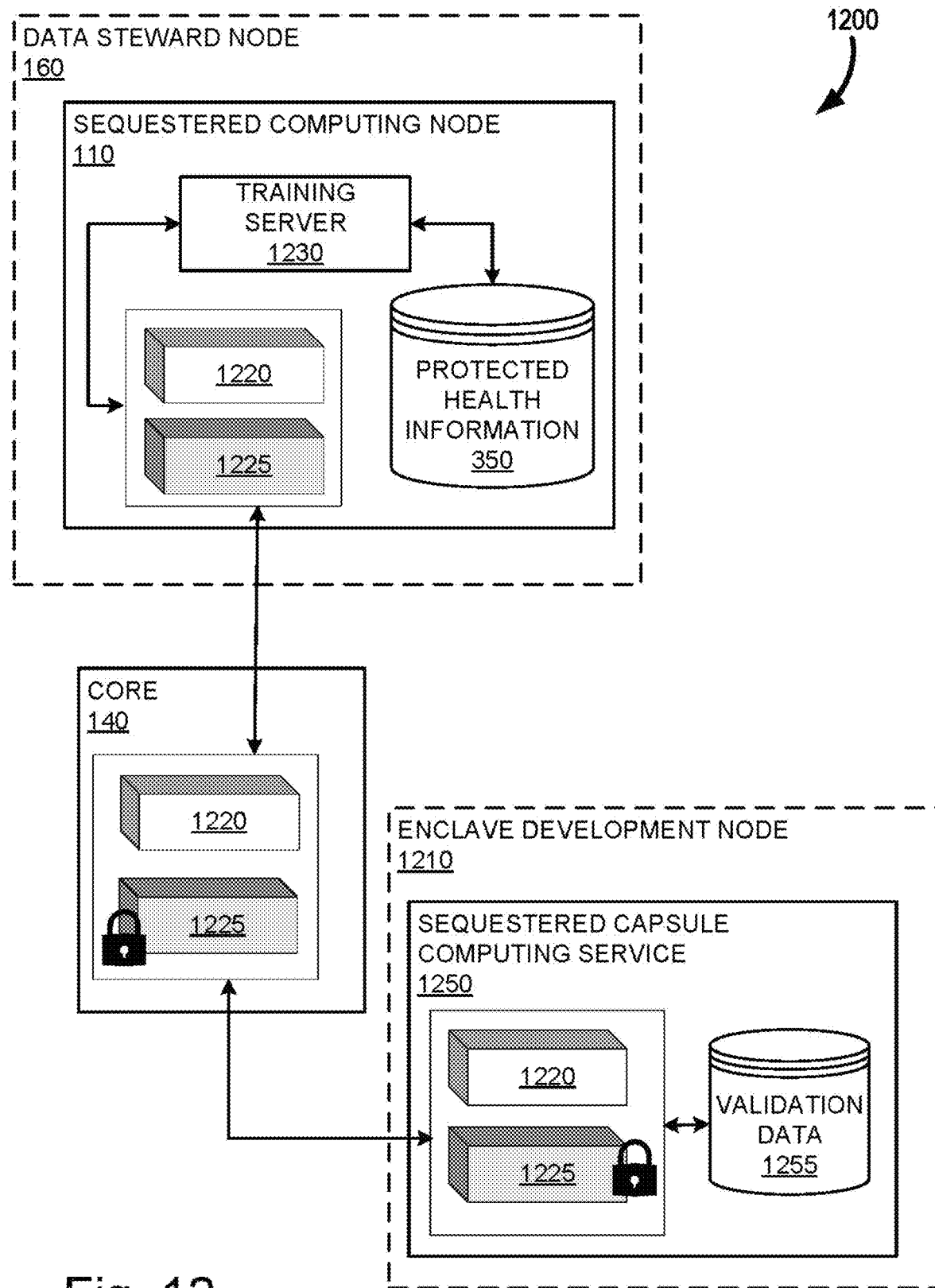
FIG. 12 is an example block diagram showing the training of the model within a zero-trust environment, in accordance with some embodiments.

Turning now to FIG. 12, a system for zero-trust training of algorithms is presented, generally at 1200. Traditionally, algorithm developers require training data to develop and refine their algorithms. Such data is generally not readily available to the algorithm developer due to the nature of how such data is collected, and due to regulatory hurdles. As such, the algorithm developers often need to rely upon other parties (data stewards) to train their algorithms. As with running an algorithm, training the algorithm introduces the potential to expose the algorithm and/or the datasets being used to train it.

In this example system, the nascent algorithm is provided to the sequestered computing node 110 in the data steward node 160. This new, untrained algorithm may be prepared by the algorithm developer (not shown) and provided in the clear to the sequestered computing node 110 as it does not yet contain any sensitive data. The sequestered computing node leverages the locally available protected health information 350, using a training server 1230, to train the algorithm. This generates a sensitive portion of the algorithm 1225 (generally the weights and coefficients of the algorithm), and a non-sensitive portion of the algorithm 1220. As the training is performed within the sequestered computing node 110, the data steward 160 does not have access to the algorithm that is being trained. Once the algorithm is trained, the sensitive portion 1225 of the algorithm is encrypted prior to being released from the sequestered computing enclave 110. This partially encrypted payload is then transferred to the data management core 140, and distributed to a sequestered capsule computing service 1250, operating within an enclave development node 1210. The enclave development node is generally hosted by one or more data stewards.

The sequestered capsule computing node 1250 operates in a similar manner as the sequestered computing node 110 in that once it is "locked" there is no visibility into the inner workings of the sequestered capsule computing node 1250. As such, once the algorithm payload is received, the sequestered capsule computing node 1250 may decrypt the sensitive portion of the algorithm 1225 using a public-private key methodology. The sequestered capsule computing node 1250 also has access to validation data 1255. The algorithm is run against the validation data, and the output is compared against a set of expected results. If the results substantially match, it indicates that the algorithm is properly trained, if the results do not match, then additional training may be required.

Figure 13:
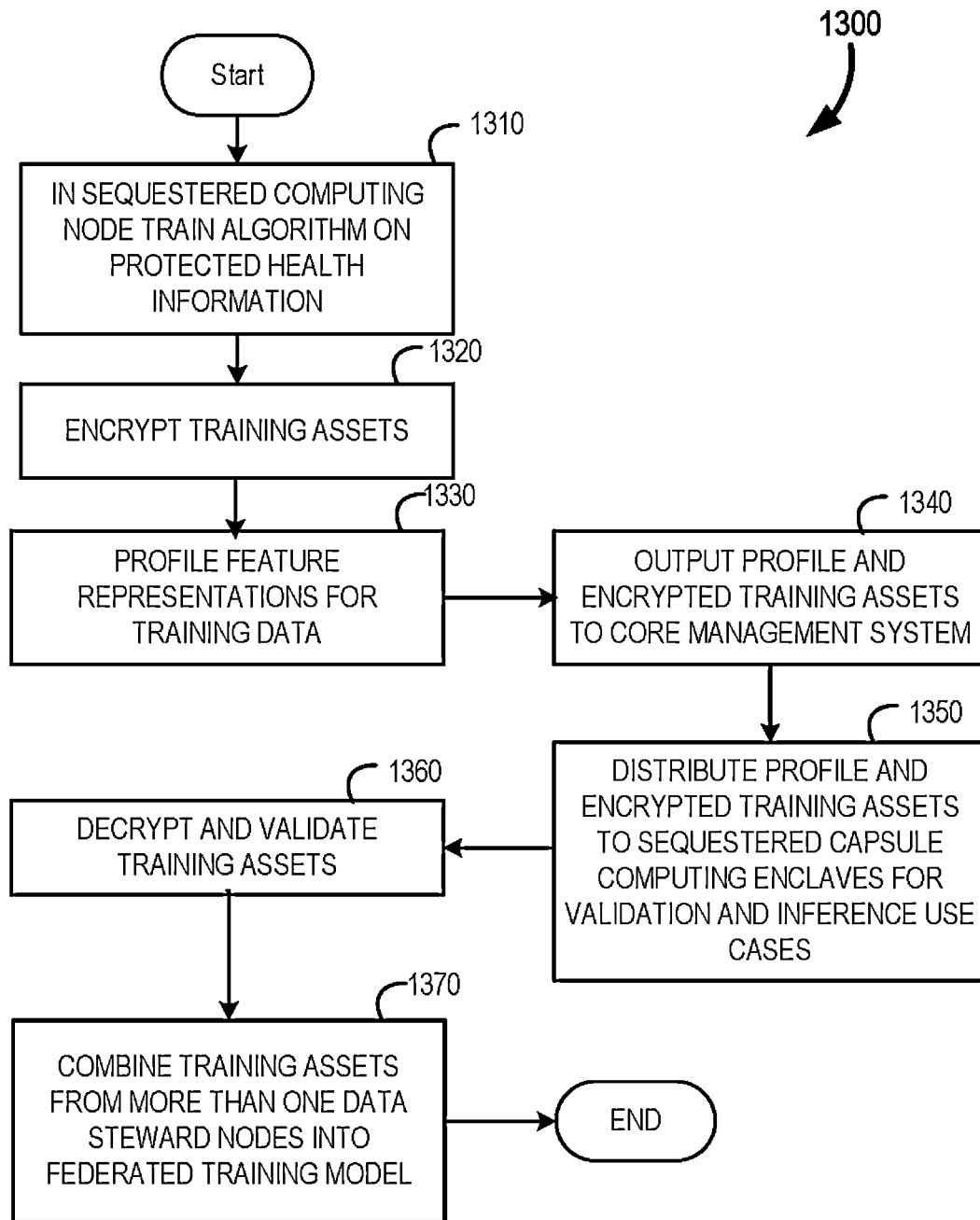
FIG. 13 is a flowchart for an example process of training of the model within a zero-trust environment, in accordance with some embodiments.

FIG. 13 provides the process flow, at 1300, for this training methodology. In the sequestered computing node, the algorithm is initially trained (at 1310). The training assets (sensitive portions of the algorithm) are encrypted within the sequestered computing node (at 1320). Subsequently the feature representations for the training data are profiled (at 1330). One example of a profiling methodology would be to take the activations of the certain AI model layers for samples in both the training and test set, and see if another model can be trained to recognize which activations came from which dataset. These feature representations are non-sensitive, and are thus not encrypted. The profile and the encrypted data assets are then output to the core management system (at 1340) and are distributed to one or more sequestered capsule computing enclaves (at 1350). At the sequestered capsule computing node, the training assets are decrypted and validated (at 1360). After validation the training assets from more than one data steward node are combined into a single featured training model (at 1370). This is known as federated training.

Figure 14:
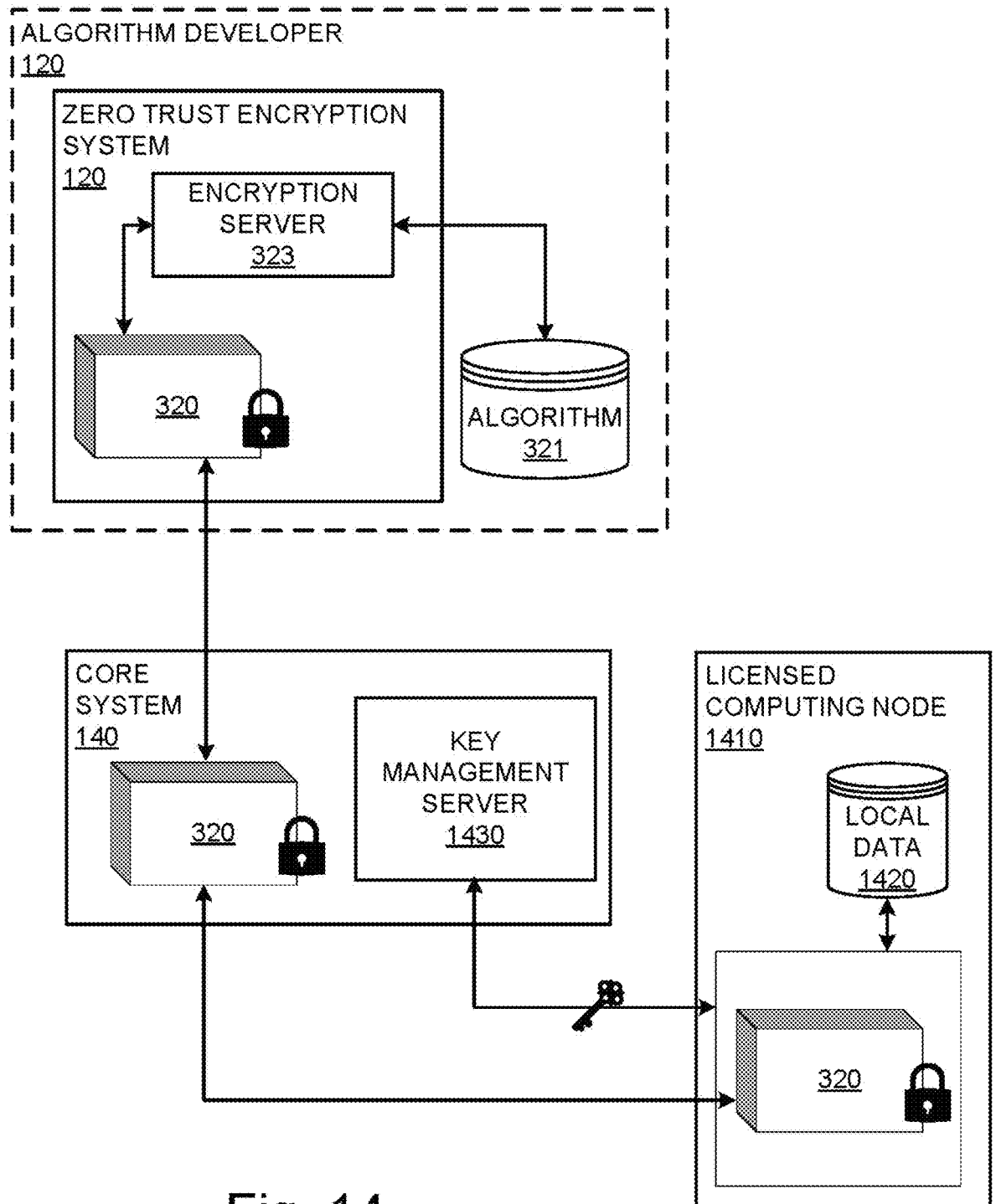
FIG. 14 is an example block diagram showing the key management for the running of an algorithm on a computing capsule within a semi-trust environment, in accordance with some embodiments.

Turning now to FIG. 14, a semi-trust computing architecture is provided, shown generally at 1300. Unlike a zero-trust system, in this example the core management system 140 operates not only as the distributer of the algorithm payloads, but also acts as a key management system. Thus, theoretically, the core management system 140 could decrypt the algorithm as it is provided. Thus, a certain level of trust is required between the algorithm developer 120 and the core management system 140. As such, it may be advantageous, in some particular embodiments, to have the core management system be hosted by the algorithm developer, or have the algorithm developer act as the key management system directly.

Regardless, in the instant embodiment, the algorithm developer's algorithm 321 is provided to the encryption server 323 to generate an encrypted payload 320. Here the entire payload is encrypted, however, as previously discussed, in alternate embodiments only a certain layer of the payload needs to be encrypted, or the payload may be separated into sensitive and non-sensitive portions and only specific portions are therefore encrypted. Regardless of method employed, the payload is provided to the core management system 140, which distributes the payload to licensed computing nodes 1410. These local nodes may include low processing powered devices that contain only local data sets. Examples of these local computing nodes may include devices such as EKG machines, dialysis machines, and other peripheral medical devices. Outside of the medical field, devices may include ATMs, smart home appliances, autonomous vehicles, or any other networked device that includes local datasets that need processing.

In addition to receiving the encrypted packet, the core management system includes a key management server 1430, which provides a key to the licensed computing node 1410 to decrypt the algorithm 320 and process local data 1420. In some embodiments, certain devices may be pre-provisioned with a key, thereby allowing the algorithm payload to be distributed without the need for a key management server by the core management system 140. This allows for deployment of the payload even when the core management system 140 cannot be contacted directly to obtain decryption keys or to confirm license validity, for example if the local environment does not have a reliable Internet connection. In some embodiments, license data may be stored on the blockchain to allow additional computing models.

Figure 15:
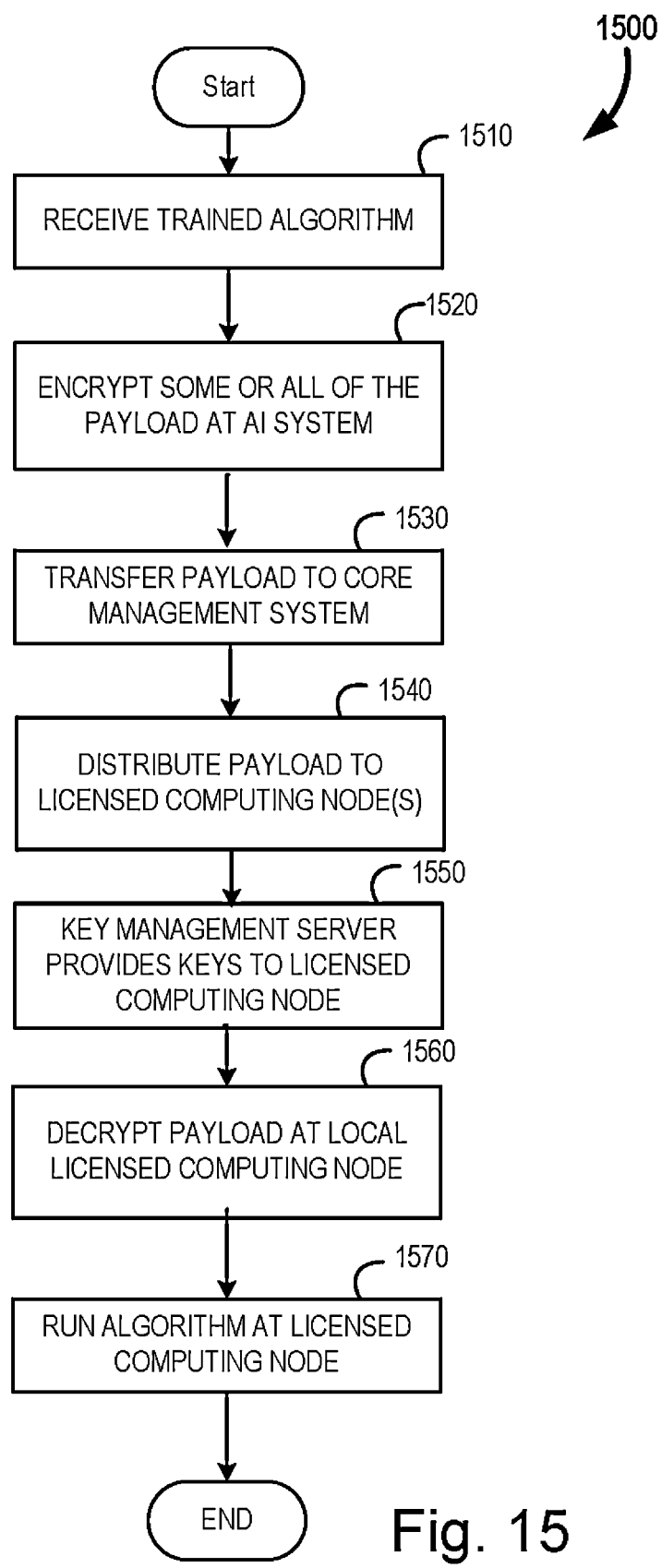
FIG. 15 is a flowchart for an example process of key management for the running of an algorithm on a computing capsule within a semi-trust environment, in accordance with some embodiments.

FIG. 15, in turn, provides an example process for deploying and running algorithms on licensed computing nodes, shown generally at 1500. In this example process, the trained algorithm is first received/generated by the algorithm developer (at 1510). This algorithm is encrypted in whole or in part (at 1520) in the zero-trust encryption node. The payload is provided to the core management system (at 1530), which then distributes it to one or more licensed computing nodes (at 1540). The key management server within the core management system provides the necessary keys to the appropriate licensed computing node(s) (at 1550). The licensed computing node(s) leverage the keys to decrypt the payload (at 1560), and run the algorithm on locally available data (at 1570).

Figure 16:
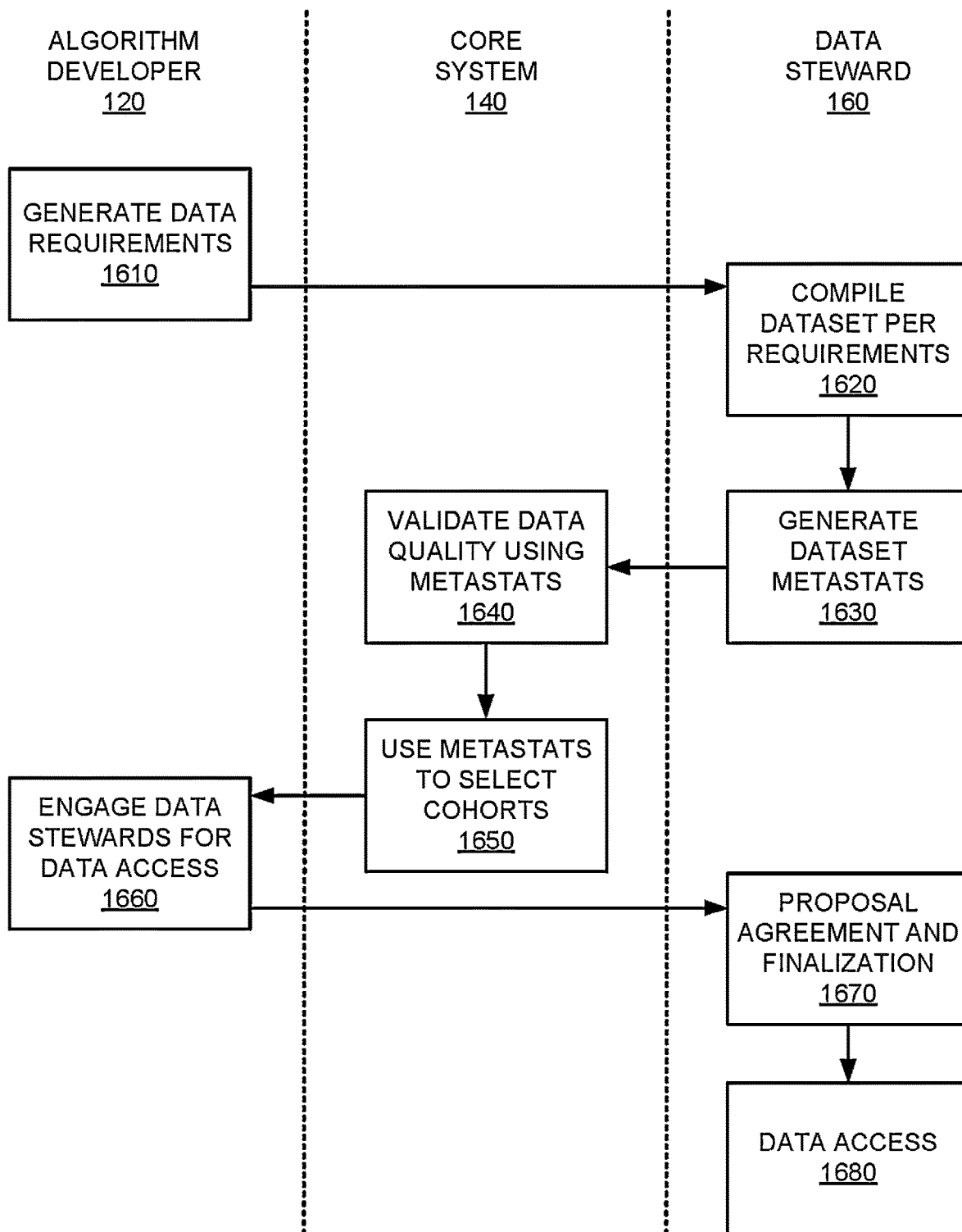
FIG. 16 is an example swim lane diagram detailing the selection of datasets between a data steward and a data consumer, in accordance with some embodiments.

Turning now to FIG. 16, a swim lane diagram for an example process of cohort selection and engagement is illustrated. In this example diagram, three parties are involved: 1) the algorithm developer 120, 2) the core management system 140, and 3) the data steward 160. While the algorithm developer 120 is illustrated in the present illustration, it should be noted that any data consumer may be seeking data from the data steward. This may include researchers, individuals involved in the set up and administration of clinical trials or other studies, and public health officials, among others. Thus, while in this, and the following Figures, reference will be made to algorithm developers as the ultimate recipient of the data, it should be recognized that this is merely for the sake of clarity and brevity, and rather any data consumer may be substituted for the algorithm developer 120.

The algorithm developer (or other party interested in a dataset) initially generates a set of data requirements (at 1610). These data requirements are generally secret, and as such are encrypted, and routed to the core management system for distribution to the various data stewards, in much the same manner that algorithms are distributed, as discussed in great detail above. The core management system may, in some embodiments, have the ability to decrypt the requirements, however in order to maintain zero-trust (or at least minimal trust) in some embodiments, the core management system is unable to decrypt the requirements.

The core management system then distributes the requirements (in some cases still encrypted) to the various sequestered computing nodes within the relevant data stewards. Once within the sequestered computing nodes, the data requirements may be decrypted and acted upon without the data steward having access to the requirement information.

Data requirements generally include a set of classes, number of required patients with each of the classes, and a total number of patients. For example, one set of data requirements could include a total of 1000 patient records, with half over the age of forty years old, and 20% of the patients African American. In other situations, the classes may be interdependent, such as a hundred patients with diabetes and of Asian descent, and fifty patients over sixty years old, of Asian descent and without diabetes, and 200 patients of any ethnicity and ages 40-70. The form of the target distribution may vary from application to application. In some applications, minimum membership of each class by total number of members, or by percentage of the total number of patients in a cohort is required. In this case, the target is a vector in which each value represents a minimum number or percentage for that class. In other applications, the objective of the aggregated datasets construction may include constraints on more than one class membership simultaneously. Each entry in the target vector may indicate a minimum number of patients in a class constructed from two underlying classes. For example, a target might be a minimum number of Asians over the age of 65, which is a single target class that is composed of underlying ethnicity and age classes.

The requirements of each class (or sets of classes when the classes are dependent upon one another) may be transformed into a vector by appending all aggregate classes together and noting the minimum desired membership (by number, percent, etc.) in each entry. To be specific, a target vector might be (100,200,100,300, . . . ) where the first entry is minimum number of Asians between 20 and 35 years of age, the next entry is minimum number of Asians between 35 and 65 years of age, then Asians over 65 years of age, females between ages 20 and 35 years of age, etc., until all the minimum memberships are enumerated.

In addition to the data requirements being provided to the sequestered computing node of the data steward, the protected health information (PHI) is likewise provided to the sequestered computing node (the same as when the data is to be processed by an algorithm). The data requirements are used to encode the data into a table of the relevant classes as fields. Each row of the table is a given patient, and each column belongs to a given class. This process of compiling the dataset according to the requirements, at 1620, greatly simplifies the generation of downstream vales used to match datasets to the data consumer's requirements.

Using the generated table, each patient record may be converted into a vector as detailed above. The entire dataset in then a set of vectors. This process of generating vectors out of the dataset is what is known as "metastats" of the dataset 1630. These metastats do not reveal significant information regarding the underlying dataset, especially is the data requirements are not known. As such the metastats may be shared with the core management system 140 without significant concern of data leakage.

Generally, the metastats may be encrypted prior to transfer to the core management system. Once received the metastats are decrypted. At this stage there may be an optional validation/verification step 1640 using these metastats to confirm data quality from the given data steward. When desired, the verification step takes the received vector set/metastats and compares it against "expected" vectors. Significant deviations (e.g., greater than a single deviation) from the expected vector may indicate a quality issue/biasing of the dataset. Expected vectors may be generated one of two ways. One method of generating an expected vector set is to collect similar dataset vectors from many different data stewards and combine them into a prototypical vector set. The second way to generate an 'expected' vector is to generate a synthetic dataset for the types of classes that are being asked for, and then converting the synthetic dataset into a series of vectors. The creation of synthetic datasets is described in considerable detail in U.S. provisional patent application No. 63/293,723 which is incorporated in its entirety herein.

After data quality verification (if desired), the metastats from the data steward are combined with metastats from other data stewards that have undergone the same process on their own PHI. The various combinations are then compared against a vector set supplied by the algorithm developer (or other party interested in receiving the data). An optimization is performed in order to minimize the difference between the target vector set and the various combinations of vector sets from the different data stewards, at 1650. When the minimum distance is determined, and when this minimum is below a set threshold, it means that the combination of those datasets/cohorts are best suited for the purposes of the data consumer. The above disclosed optimization step may be subject to a cost function, which applies penalties to certain combinations of data stewards. These costs may be based upon data quality measures (as determined above), actual monetary cost per patient for the records, a cost function against using records from too many (or too few) data stewards, location diversity of the patient cohorts, and the like.

In the above described optimization process, the core management system has access to the metastats for the various data stewards and the target vector sets for the data consumer's study/research/algorithm. Without knowing the data requirements, this renders much of the data meaningless to the core management system 140, thus reinforcing the zero-trust (or at least minimal trust) nature of the system. However, in other embodiments, the data stewards' metastats may be homomorphically encrypted, as is the target vector set from the algorithm developer (or other data consumer). Data encrypted in homomorphic space may have computations performed on them without the need for decryption. As such, the vector optimization process may be performed in the core management system without ever needing (or being able to) decrypt the underlying vectors. In this regard, the system is truly a zero-trust environment. In this methodology, all data stewards use the same homomorphic encryption key and are able to decrypt the recommended cohort definition from the optimization. To be specific, each data steward will receive an encrypted vector (the "cohort specification vector") that determines what admixture of their patients (a fixed sample fractional sample from the total, or a combination of sampled individuals with specific class memberships, for example) should be used in the validation. Since the data steward has the encryption key, it is possible to decrypt and apply this selection criterion. Despite the fact that multiple data stewards have the same decryption key, the system is still zero-trust because they never get access to each other's metadata or cohort specification vector.

In another embodiment, a standard secure multiparty computation (SMPC) scheme is used to combine the metadata and optimize the final cohort selection from each data steward. This approach also prevents the core management system from seeing data steward secrets, and has the added advantage that individual data stewards can't decrypt each others' data.

After the selection of the best data stewards' data is made, this information is passed back to the algorithm developer (or other data consumer). The data consumer may then engage with the data steward(s) directly to gain access to the data, at 1660. Gaining access to PHI is not a trivial matter and requires the data steward and the data consumer to agree to terms and conditions, execute agreements to properly maintain and protect the data, and the like, at 1670. Finally, after all this is completed, the correct datasets are transferred, or made accessible to, the data consumer, at 1680.

Figure 17:
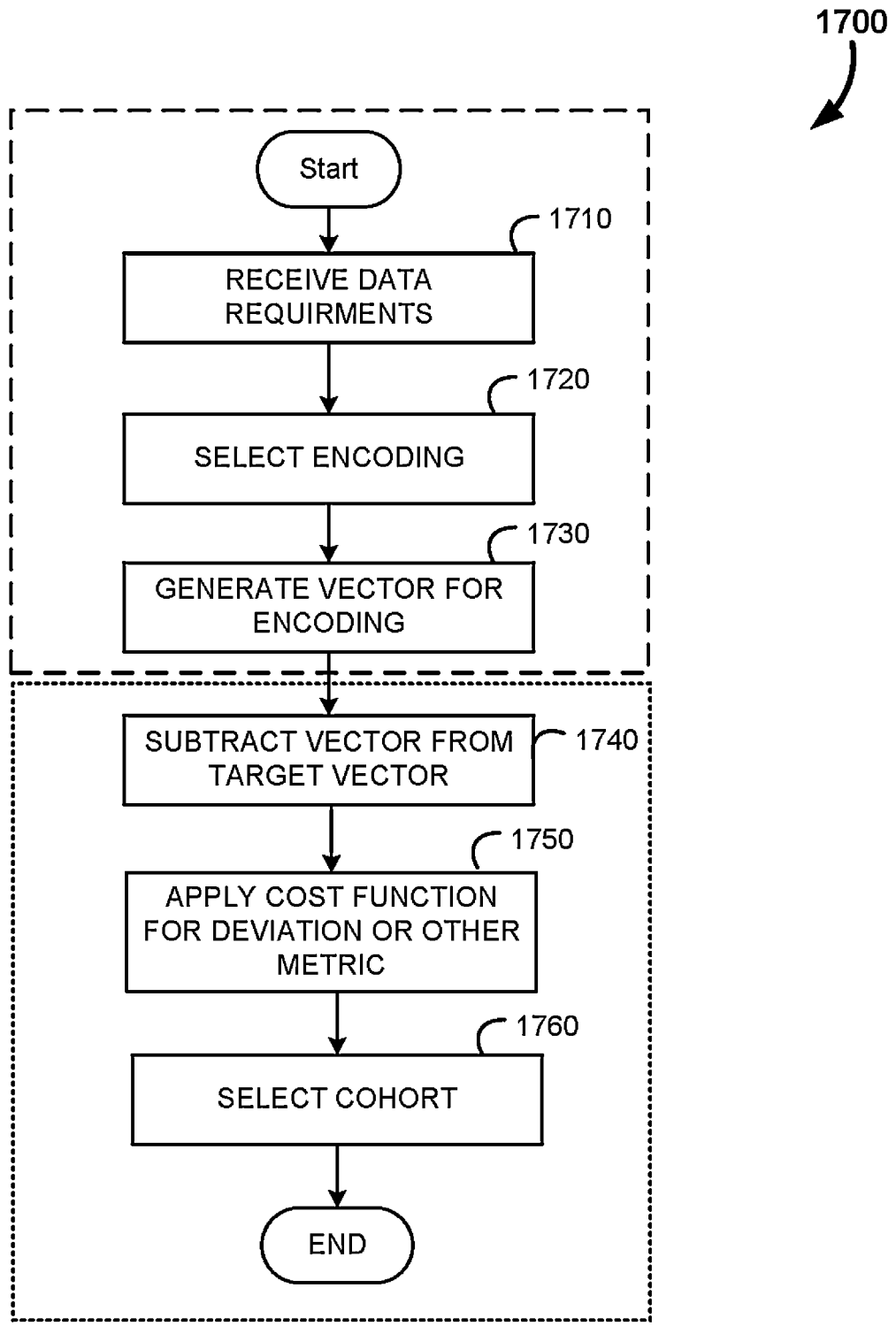
FIG. 17 is a flowchart for an example process of cohort selection, in accordance with some embodiments.

Turning now to FIG. 17, a flow chart for an example process of cohort selection is provided, at 1700. For clarity purposes, the dashed outlined box around steps 1710, 1720 and 1730 indicates that these steps occur within the sequestered node of the data steward. Conversely, the dotted lined box around steps 1740, 1750 and 1760 indicate that these steps are completed in the core management system.

As noted before, the data steward received a set of requirements for the data from the data consumer (at 1710). These requirements indicate which classes (or sets of classes) the data consumer is interested in, and in some embodiments, the number of individuals in each class(es) that are required. In some embodiments, providing the number of patients in each class(es) may not be desirable as it may allow the data steward to "cherry-pick" their data. Further in this disclosure are provided methods for verifying that data is not cherry-picked, but in some cases, by not even letting the data steward know what data is desired, and only the metrics by which to generate metastats for it, the ability to cherry-pick the data is entirely removed. In other embodiments, it is actually of benefit for the data consumer to provide exactly the numbers of patients needed for each class (or groups of classes), as meeting these quotas using a general dataset will be all but impossible. In these situations the data stewards are heavily incentivized to down sample their datasets to provide relevant data that fits the data consumer's requirements. Here, cherry picking (and conversely picking adversarial patient subsets) is a paramount concern. For these reasons, further in this disclosure are presented methods for verifying the data fidelity.

After the requirements have been received (as an encrypted file) the requirements may be decrypted within the secure computing node. This means that the data steward itself is never privy to the data consumer's requirements— further reinforcing the zero-trust environment. The requirements, once decrypted, may be applied to the data that is available within the secure computing node to encode it (at 1720) in a tabular format, as discussed previously. Once the data is tabulated in the proper manner, the vector/metastats for the data is generated (at 1730).

The metastats are then encrypted and provided to the core management system for optimization against the target vector set supplied by the data consumer. Once the metastats are received, by the core management system they may be decrypted for processing, or as mentioned earlier, may remain homomorphically encrypted and processed without ever being decrypted. The determination of which patient cohorts to select is based upon an optimization to minimize the difference between the target vector set versus any combination of data steward vector sets (at 1740).

In some embodiments, T is a function that converts a set of patient data into a series of subsets and counts. Thus, the function to select which data stewards' data to use is given as:

$$\text{Goal} = \text{minimize} \| T\{\text{target}\} - T(\text{Union}(\{\text{data steward}\})) \| \quad \text{Equation 1}$$

As noted previously, this optimization equation may be further subjected to a cost function (at 1750). The cost function may provide a penalty to certain conditions. The degree and type of penalty may be configured by the data consumer. For example, a pharmaceutical company engaging in a clinical trial may not have much monetary cost sensitivity but may be very interested in having geographically diverse patient sets. Such a company may not have a penalty associated with price of data but may penalize having data stewards that are providing too large a share of the data and/or are located in the same general region. Conversely, a university study may be very sensitive to monetary costs and may thus penalize data sets that are more expensive. Such a cost function $f(x)$ may be applied as follows:

$$\text{Cost} = f(\text{Union}(\{\text{data steward data}\})) \quad \text{Equation 2}$$

This represents a cost for assembling a group of data steward datasets. For example, if the cost of assembling a dataset depends only upon the number of patients in the dataset, but varies by data steward, then the functional form for f would be:

$$f = \text{sum}_j(P_j N_j) \quad \text{Equation 3}$$

where j is a sum over data stewards with total number of patients N and cost per patient P. Alternatively, the cost could depend on class membership and data steward, in which case we would have:

$$f = \text{sum}_i(\text{sum}_j(P_{ij} * N_{ij})) * \text{normalization} \quad \text{Equation 4}$$

where i is a sum over classes in the target vector, j is a sum over data stewards, and normalization is a normalization factor that depends on the number of patients double-counted in a sum over i.

Given any $f$, the optimization of the selection of data steward data sets is:

$$\text{Argmin}_w f(w) \text{ subject to the constraint that } \text{sum}_{jc} (N_{cj} * w_j) > \text{Target} c \quad \text{Equation 5}$$

for all classes c, where j is a sum over data stewards, N is the number of patients in class c and w is the weighting vector for data steward subset selection.

After the optimization has been completed, the core management system yields a set of data stewards that, when their data sets are combined, are best suited to achieve the needs of the data consumer. These patient cohorts/datasets are selected (at 1760) and the information around these data sets are provided to the data consumer. The data consumer is then able to contact the data stewards directly in order to execute the needed agreements to gain access to the data and/or patient lists. In some other embodiments, the core management system may act as a data escrow to assist in the transfer of information. In yet other embodiments, the data consumer is never informed of which data stewards are best suited to meet their needs. Rather, the core management system acts as a broker to receive the payment from the data consumer, collect the various data sets from the data steward (s), and facilitate transfer of the data. In some cases, the identity of the data steward is never revealed to the data consumer, and vis versa. In circumstances where the core management system acts as a broker in this manner, an additional fee may be applied for the logistical services being provided.

Figure 18:
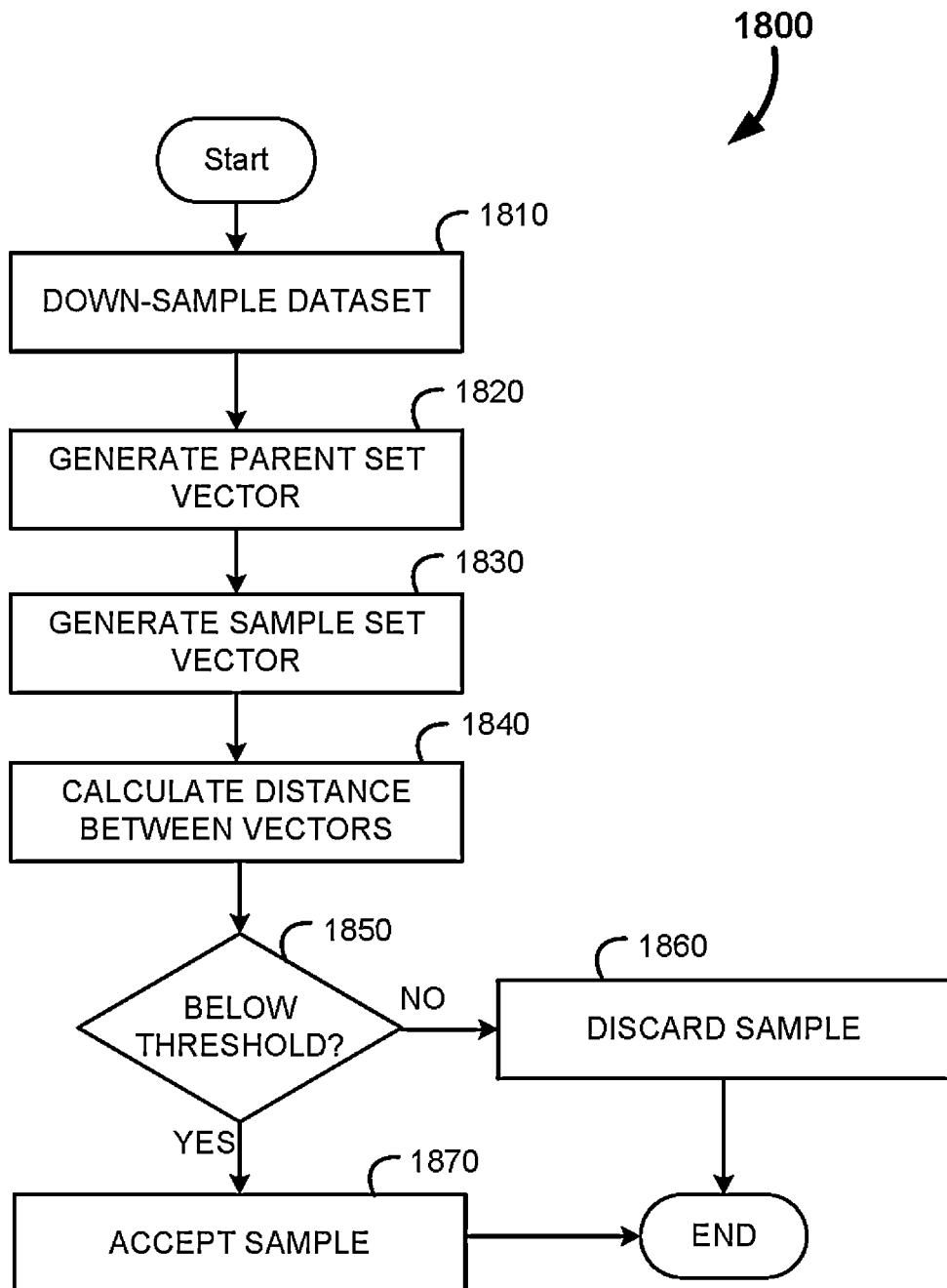
FIG. 18 is a flowchart for an example process of sample acceptance for a down sampling or curated dataset, in accordance with some embodiments.

Turning now to FIG. 18, a method is provided for the verification of a dataset, shown at 1800. This verification is particularly useful when the data steward is providing a subset of their data to a data consumer. This often occurs when a specific set od data requirements need to be met, and the larger dataset does not comport to the requirements, but a selected subset of the larger dataset could meet the needs of the data consumer. This process is known as down sampling. Down sampling has certain problems however—it is easily possible to introduce biases into the sample set when down sampling (either intentionally or unintentionally). This may result in cherry-picking "desirable" data, or conversely may select data that is "bad" for the study results.

Generally, a regulatory agency, such as the Food and Drug Administration (FDA), is very concerned that a dataset is cherry-picked for a given clinical trial (for example). Such cherry-picking may result in the procedure/product/treatment being shown to be more effective and/or safer than it actually is. Conversely, the data consumer may be concerned that data that is selected to be adversarial to their study/trial. This may result in the product or treatment being rejected as not being affective or safe. Thus, a robust means for verifying data is needed.

In this example process, the data steward first down samples their dataset (at 1810). Any acceptable down sampling methodology may be employed for this step. A vector set is generated for the full/parent dataset (at 1820). Vector generation may be performed in the same manner as described above. Similarly, a vector set may be generated for the child sample set (at 1830). Again, vector generation is performed as previously discussed.

Although not shown, in some embodiments, the vector values for the child sample set may be adjusted by known cross elasticities. For example, individuals of African descent are known to have a higher rate of heart disease. This is a well-established, statistically quantified, cross elasticity. If the classes include race and heart disease, and the child sample is fifty percent African American, whereas the parent set is only twenty percent African American (due to data consumer requirements for example), there will be a noticeable increase in the percentage of heart disease in the sample set. Since the elasticity between the forced variable (here race) and the biased variable (here heart disease instances) is known, the resulting vector set may be adjusted to take into account this relationship.

After vectors are generated (and in some cases adjusted), the distance between the two vector sets is calculated (at 1840). The results of the distance measurement are then compared against a threshold number (at 1850). This threshold may be a configured absolute number, or a statistically defined amount (e.g., one standard deviation, etc.). If the difference is above the threshold, then the sample is clearly out of line with the parent dataset and should be discarded (at 1860). However, if the difference is small enough/below the threshold, then the data is known to be an accurate representation of the larger dataset and trustworthy. This sample may then be accepted for downstream usage (at 1870). An example of computing such a distance and determining a threshold for a representative sample is to frame the distance as a p-value in a hypothesis test. There are a number of different hypothesis testing algorithms (e.g., Anderson-Darling Statistic, t-test, F-test, one-tailed z-score, and many others) that can be used to compare a sample distribution to a parent distribution. When the p-value is above a threshold (for example, 0.75), then the sample can be interpreted to be a fair representation of the underlying distribution. In cases in which the sample is large compared to the underlying distribution and/or when the algorithm developer's validation depends on high performance on the sample set, then a higher p-value threshold would be used.

Figure 19:
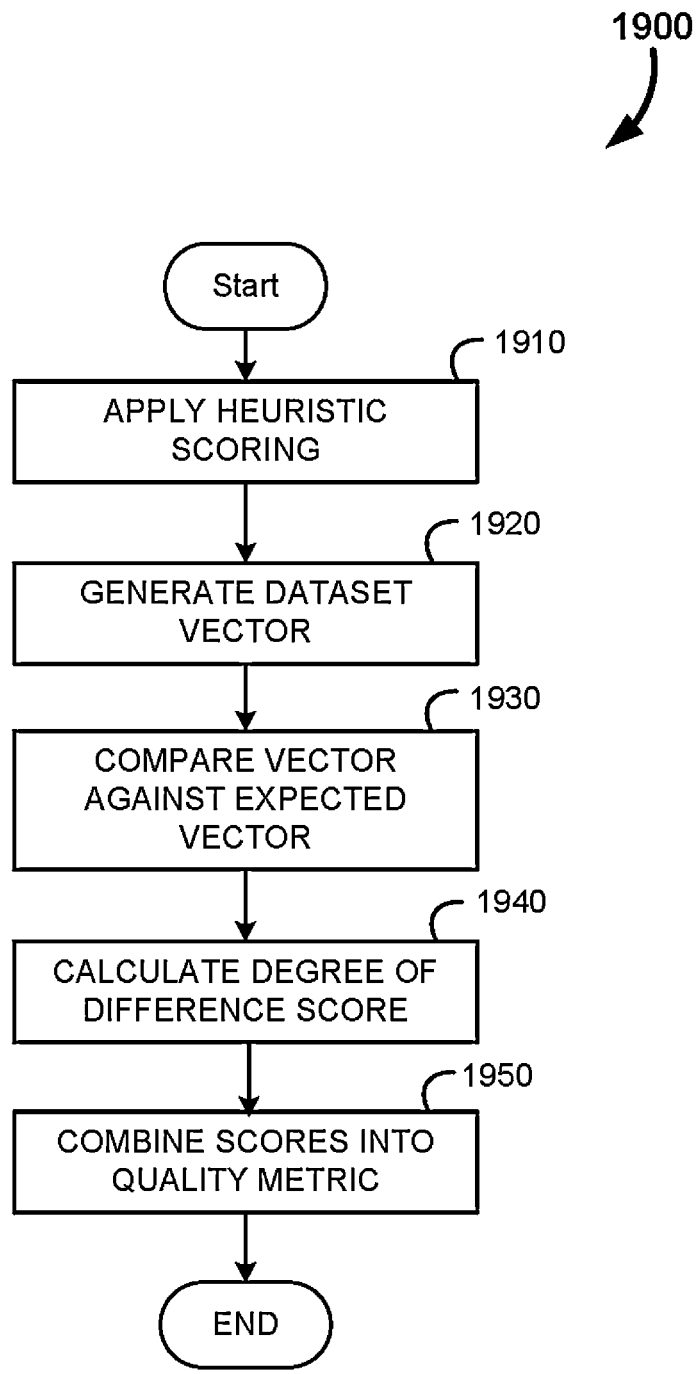
FIG. 19 is a flowchart for an example process of dataset quality metric generation, in accordance with some embodiment.

Turning to FIG. 19, a flow chart for the example process of scoring the quality of a dataset is provided at 1900. Dataset quality is generally a difficult thing to quantify, and yet has enormous implications for a study or clinical trial. With poor data, the study may fail, or possibly worse, yield false results. Clinical trials are expensive to perform, and often have millions (if not hundreds of millions) of dollars of R&D funding at stake. As such, the ability to qualify if a dataset is "good" or not may be of significant value.

The first step in determining dataset quality is to perform a heuristic scoring methodology to the data (at 1910). This scoring may employ rule-based queries that identify tell-tale signs of erroneous or "sloppy" data collection and/or recordation. For example, missing values, negative values, and values outside a possible range for the variable (a temperature of 976 degrees for example) may all be identified. The frequency/count of these kinds of errors may be tabulated, and a percentage of the total data that includes these errors calculated. This percentage may be the raw score, after applying a configured weight. Alternatively, the percentage may be compared against one or more thresholds, and thus bucketed into categories. Each category may be assigned a score.

After the heuristic scoring, a vector-based scoring approach may be applied. This starts with the generation of a vector set for the data (at 1920). This vector generation is the same method as already discussed in some considerable detail. This vector set is then compared against a set of expected vectors (at 1930). As noted previously, the expected vector set may be generated in a number of ways. One manner in which it may be generated is to utilize a synthetic dataset that is generated for the given dataset classes. This synthetic data may be used to generate a vector set. Alternatively, the expected vector set may be an amalgamation of different vector sets from different data stewards with the same, or substantially similar, datasets. This aggregated dataset then becomes the gold standard vector set.

Regardless of how the expected vector set is generated, when it's compared against the vector set for the current dataset that is being scored, a distance function is employed. As noted before, the distance function may include Anderson-Darling Statistic, t-test, F-test, one-tailed z-score, among many others, which calculates a degree of difference between the two sets. This degree of difference may be weighted in order to generate a second part of the quality metric score (at 1940). Alternatively, as with the heuristic scoring methodology, it may be possible to set a series of thresholds for the degrees of difference between the vector sets. This allows the vector comparison to be bucketized into classes/groupings based upon how divergent the two sets are.

Regardless of how the two scores are generated, they may be combined together to render a final quality metric (at 1950). The combination step may be a simple addition of the weighted scores, an averaging of the scores, and/or a normalization step between the scores followed by them being multiplied together. In some embodiment, the combined scores are represented as a percentage. In other embodiments, the scores may be normalized to a point scale, and rounded to yield a "star" or other point-based result (e.g., 9 out of 10 quality, three star quality, gold level quality, etc.).

Figure 20:
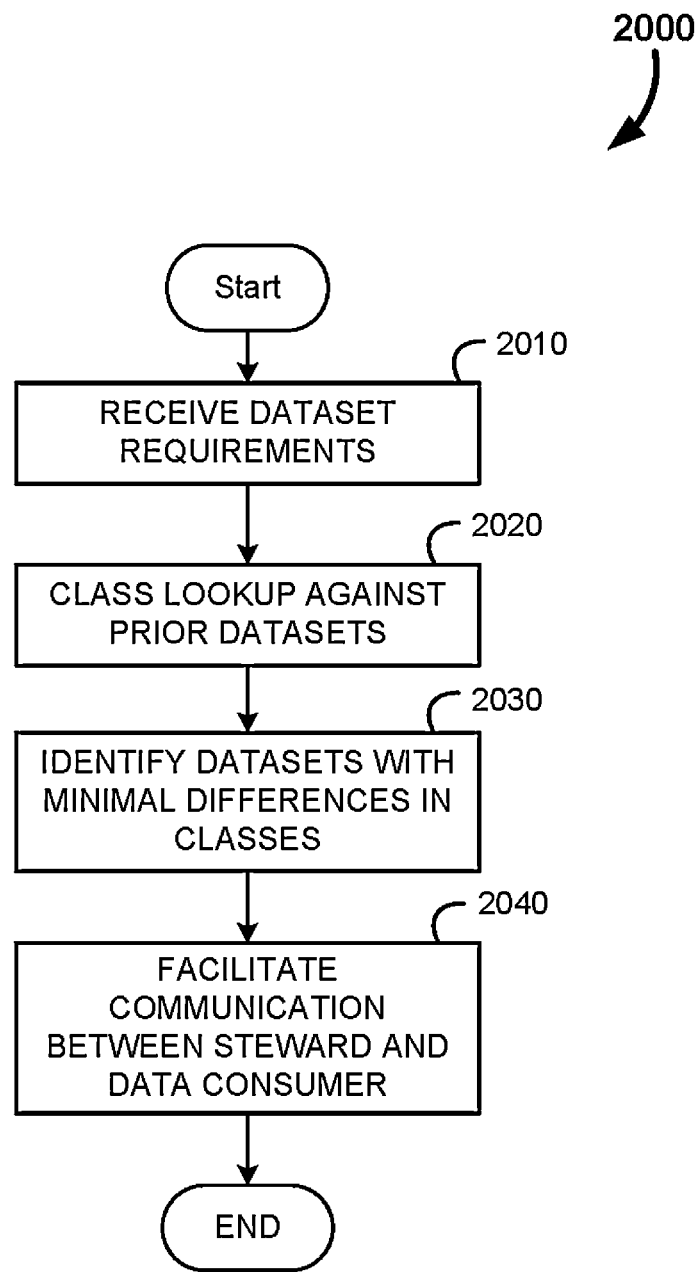
FIG. 20 is a flowchart for an example process of dataset recommendation, in accordance with some embodiments.

Turning now to FIG. 20, a flow diagram for an example process for recommending a dataset to a data consumer based upon historical knowledge is provided at 2000. As the core management system is, in some embodiments, exposed to many dataset vector sets, it is possible that this information may be retained for future lookup. In some embodiments, it may be valuable for a data consumer to have a dataset recommended to them without the need for a full selection optimization process. This is especially true when the dataset has already been vetted, and is known to be of high quality.

In this example process the dataset requirements are received in the core management system from the data consumer (at 2010). The core management system then queries the records it maintains of vector values for prior datasets. Particularly, the classes of the prior datasets may be queried and compared against the requirements (at 2020). The difference between the required classes and the available classes are determined, and the datasets with "minimum" differences between the requirements and the existing classes are identified (at 2030). This minimum difference may be a simple count, in some embodiments. For example, assume the required dataset includes age, ethnicity, weight, blood cell count, and blood type. Also assume a dataset exists with age, ethnicity, weight, and blood type. The difference between these two datasets is only a single field, and thus this may be considered a very close match. In alternate embodiments, however, the number of similar fields may not be the only consideration. Rather, each class may be assigned a numerical weight based upon the difficulty to procure the class data. So, for instance, the patients' blood type is generally simple to procure (all that is needed is a simple blood draw). This class may then be assigned a relatively low numerical weight. Similarly, basic vitals and profile data may also be assigned low numerical weights (e.g., age, gender, ethnicity, weight, height, blood pressure, etc.). However, some classes may be much harder to collect (e.g., neutrophile count as a longitudinal time series). Such a class may be assigned a larger numerical weight.

In this embodiment, the count of different classes between the required classes and the available classes in a known dataset may be adjusted by the weights, and a summation of the resulting adjusted counts may determine the distance between the classes. Thus, a dataset missing five (for example) of the classes that are easily determined may be found to be closer to the required dataset than a know dataset only missing a single class, but the class is very difficult to obtain. Another example of this is a requirement for a dataset that includes 30% of the records to be of Native American descent and over the age of 60, as well as a host of other profile information. As finding a dataset with such a large percentage of Native American's is extremely rare, if one exists that meets this criterion (even if it lacks all the other desired profile information) it may still be ranked as very close to the required dataset, even as compared to datasets that match all other classes yet have the ethnicity class incongruent to the required dataset.

Regardless of method utilized to determine differences between known datasets and the required one, once it has been identified, the core management system may facilitate the connection of the data steward for the known dataset with the data consumer (at 2040). This may simply include providing the data consumer an identifier of which dataset is of interest and the data steward's contact information, or may be more involved process, where the core management system acts as a broker between the two entities.

Figure 21A:
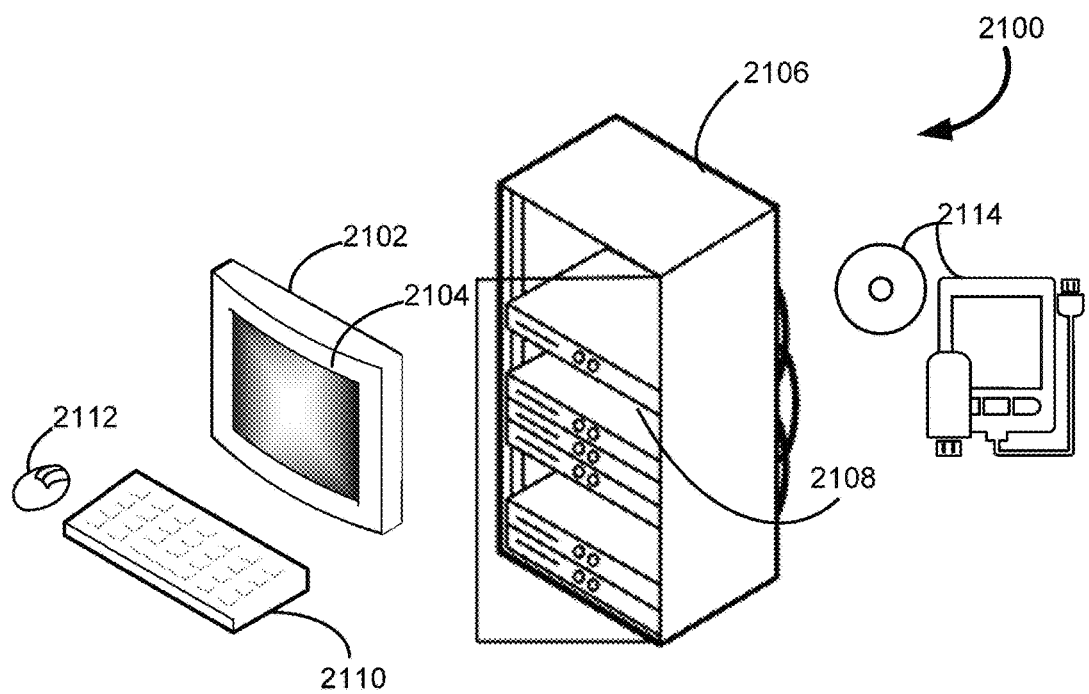
FIGS. 21A and 21B are illustrations of computer systems capable of implementing the dataset selection, verification and recommendation, in accordance with some embodiments.
Figure 21B:
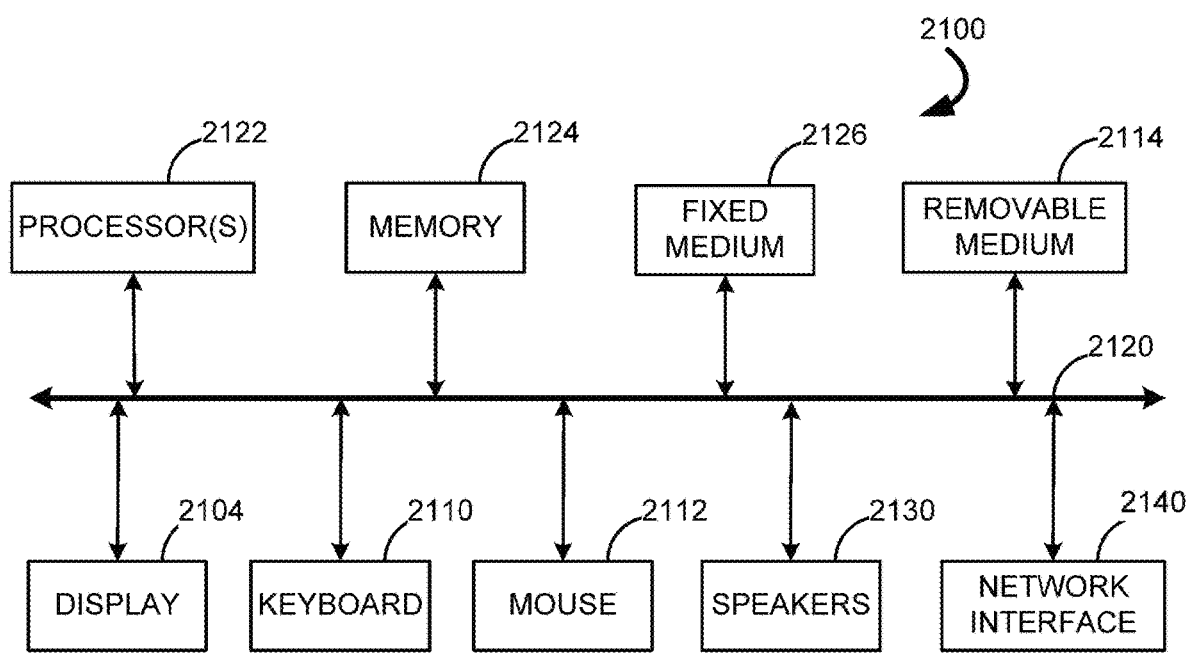

Now that the systems and methods for dataset selection optimization have been provided, attention shall now be focused upon apparatuses capable of executing the above functions in real-time. To facilitate this discussion, FIGS. 21A and 21B illustrate a Computer System 2100, which is suitable for implementing embodiments of the present invention. FIG. 21A shows one possible physical form of the Computer System 2100. Of course, the Computer System 2100 may have many physical forms ranging from a printed circuit board, an integrated circuit, and a small handheld device up to a huge super computer. Computer system 2100 may include a Monitor 2102, a Display 2104, a Housing 2106, server blades including one or more storage Drives 2108, a Keyboard 2110, and a Mouse 2112. Medium 2114 is a computer-readable medium used to transfer data to and from Computer System 2100.

FIG. 21B is an example of a block diagram for Computer System 2100. Attached to System Bus 2120 are a wide variety of subsystems. Processor(s) 2122 (also referred to as central processing units, or CPUs) are coupled to storage devices, including Memory 2124. Memory 2124 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable form of the computer-readable media described below. A Fixed Medium 2126 may also be coupled bi-directionally to the Processor 2122; it provides additional data storage capacity and may also include any of the computer-readable media described below. Fixed Medium 2126 may be used to store programs, data, and the like and is typically a secondary storage medium (such as a hard disk) that is slower than primary storage. It will be appreciated that the information retained within Fixed Medium 2126 may, in appropriate cases, be incorporated in standard fashion as virtual memory in Memory 2124. Removable Medium 2114 may take the form of any of the computer-readable media described below.

Processor 2122 is also coupled to a variety of input/output devices, such as Display 2104, Keyboard 2110, Mouse 2112 and Speakers 2130. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, motion sensors, brain wave readers, or other computers. Processor 2122 optionally may be coupled to another computer or telecommunications network using Network Interface 2140. With such a Network Interface 2140, it is contemplated that the Processor 2122 might receive information from the network, or might output information to the network in the course of performing the above-described zero-trust computing. Furthermore, method embodiments of the present invention may execute solely upon Processor 2122 or may execute over a network such as the Internet in conjunction with a remote CPU that shares a portion of the processing.

Software is typically stored in the non-volatile memory and/or the drive unit. Indeed, for large programs, it may not even be possible to store the entire program in the memory. Nevertheless, it should be understood that for software to run, if necessary, it is moved to a computer readable location appropriate for processing, and for illustrative purposes, that location is referred to as the memory in this disclosure. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable medium." A processor is considered to be "configured to execute a program" when at least one value associated with the program is stored in a register readable by the processor.

In operation, the computer system 2100 can be controlled by operating system software that includes a file management system, such as a medium operating system. One example of operating system software with associated file management system software is the family of operating systems known as Windows® from Microsoft Corporation of Redmond, Washington, and their associated file management systems. Another example of operating system software with its associated file management system software is the Linux operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is, here and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may, thus, be implemented using a variety of programming languages.

In alternative embodiments, the machine operates as a standalone device or may be connected (e.g., networked) to other machines. In a networked deployment, the machine may operate in the capacity of a server or a client machine in a client-server network environment or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, Glasses with a processor, Headphones with a processor, Virtual Reality devices, a processor, distributed processors working together, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies of the presently disclosed technique and innovation.

In general, the routines executed to implement the embodiments of the disclosure may be implemented as part of an operating system or a specific application, component, program, object, module or sequence of instructions referred to as "computer programs." The computer programs typically comprise one or more instructions set at various times in various memory and storage devices in a computer (or distributed across computers), and when read and executed by one or more processing units or processors in a computer (or across computers), cause the computer(s) to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention. It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A computerized method for recommending a dataset in a zero-trust environment, the method comprising:
- receiving a set of dataset requirements as a required vector set;
- generating historical vector sets, wherein each vector set corresponds to a known dataset, wherein the generating the historical vector sets is performed in a sequestered enclave comprising a virtual machine running on secure computing processors;
- querying the historical vector sets;
- aggregating a plurality of permutations of historical vector sets into aggregated vectors, wherein the aggregating combines the historical vector sets into the aggregated vector by appending aggregated classes together;
- selecting the aggregated vector via an optimization, wherein the optimization is responsive to a minimized distance between the aggregated vector and the required vector set, wherein the distance is a calculated difference;
- identifying a patient cohort from the aggregated vector;
- brokering contact between a data consumer and a data steward to enable access to the identified patient cohort, wherein the access includes at least one of research on the patient cohort, screening the patient cohort for a pathology, screening the patient cohort for a medical intervention.

2. The method of claim 1, wherein the calculating the difference is by framing the distance as a p-value in a hypothesis test, compared against a threshold.

3. The method of claim 1, wherein the difference is calculated as a count of differing classes.

4. The method of claim 1, wherein the difference is calculated as a numerically weighted summation of differing classes.

5. The method of claim 1, wherein the dataset requirements are healthcare data and the known dataset is healthcare data.

6. The method of claim 1, wherein the optimization includes a penalty function for at least one of monetary cost, location of patients associated with the data, and source of data.

7. A zero-trust computing system for recommending a dataset, the system comprising:
- a data store for receiving a set of dataset requirements as a required vector set; and
- a runtime server hosted within a sequestered enclave comprising a virtual machine running on secure computing processors for generating historical vector sets, wherein each vector set corresponds to a known dataset, querying the historical vector sets; calculating the difference between the required vector set and each of the historical vector sets; aggregating a plurality of permutations of historical vector sets into aggregated vectors, wherein the aggregating combines the historical vector sets into the aggregated vector by appending aggregated classes together, selecting the aggregated vector via an optimization, wherein the optimization is responsive to a minimized distance between the aggregated vector and the required vector set, wherein the distance is a calculated difference, identifying a patient cohort from the aggregated vector, brokering contact between a data consumer and a data steward to enable access to the identified patient cohort, wherein the access includes at least one of research on the patient cohort, screening the patient cohort for a pathology, screening the patient cohort for a medical intervention.

8. The system of claim 7, wherein the calculating the difference is by framing the distance as a p-value in a hypothesis test, compared against a threshold.

9. The system of claim 7, wherein the difference is calculated as a count of differing classes.

10. The system of claim 7, wherein the difference is calculated as a numerically weighted summation of differing classes.

11. The system of claim 7, wherein the dataset requirements are healthcare data and the known dataset is healthcare data.

12. The system of claim 7, wherein the optimization includes a penalty function for at least one of monetary cost, location of patients associated with the data, and source of data.

13. A computer program products stored on non-volatile computer memory which when executed upon a computer system performs the steps of:
- receiving a set of dataset requirements as a required vector set;
- generating historical vector sets, wherein each vector set corresponds to a known dataset by encoding the dataset according to a set of classes, generating a matrix of the encoded dataset and converting the generated matrix into a series of points in a vector space, and wherein the generating the historical vector sets is performed in a sequestered enclave comprising a virtual machine running on secure computing processors;
- querying the historical vector sets;
- aggregating a plurality of permutations of historical vector sets into aggregated vectors, wherein the aggregating combines the historical vector sets into the aggregated vector by appending aggregated classes together;
- selecting the aggregated vector via an optimization, wherein the optimization is responsive to a minimized distance between the aggregated vector and the required vector set, wherein the distance is a calculated difference;
- identifying a patient cohort from the aggregated vector;
- brokering contact between a data consumer and a data steward to enable access to the identified patient cohort, wherein the access includes at least one of research on the patient cohort, screening the patient cohort for a pathology, screening the patient cohort for a medical intervention.

14. The computer program product of claim 13, wherein the calculating the difference is by framing the distance as a p-value in a hypothesis test, compared against a threshold.

15. The computer program product of claim 13, wherein the difference is calculated as a count of differing classes.

16. The computer program product of claim 13, wherein the difference is calculated as a numerically weighted summation of differing classes.

17. The computer program product of claim 13, wherein the dataset requirements are healthcare data and the known dataset is healthcare data.

18. The computer program product of claim 13, wherein the optimization includes a penalty function for at least one of monetary cost, location of patients associated with the data, and source of data.

* * * * *